United States Patent
Yano et al.

(10) Patent No.: US 8,958,165 B2
(45) Date of Patent: Feb. 17, 2015

(54) CYANINE COMPOUND AND OPTICAL FILTER AND OPTICAL RECORDING MATERIAL CONTAINING SAME

(75) Inventors: Toru Yano, Tokyo (JP); Mitsuhiro Okada, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 1075 days.

(21) Appl. No.: 12/523,186

(22) PCT Filed: Mar. 28, 2008

(86) PCT No.: PCT/JP2008/056036
§ 371 (c)(1),
(2), (4) Date: Jul. 15, 2009

(87) PCT Pub. No.: WO2008/123404
PCT Pub. Date: Oct. 16, 2008

(65) Prior Publication Data
US 2010/0003445 A1    Jan. 7, 2010

(30) Foreign Application Priority Data

Mar. 30, 2007 (JP) ................................ 2007-091012
Mar. 13, 2008 (JP) ................................ 2008-063414

(51) Int. Cl.
G02B 5/22       (2006.01)
G11B 7/2472    (2013.01)
C07D 209/08    (2006.01)
C07D 209/14    (2006.01)
C07D 209/18    (2006.01)
C07D 209/20    (2006.01)
C07D 209/42    (2006.01)
C07D 209/60    (2006.01)
C07D 405/14    (2006.01)
C07D 409/14    (2006.01)
C07D 413/06    (2006.01)
C07D 417/06    (2006.01)
C09B 23/04     (2006.01)
C09B 23/06     (2006.01)
C09B 23/08     (2006.01)
C09B 45/20     (2006.01)

(52) U.S. Cl.
CPC ............ *G11B 7/2472* (2013.01); *C07D 209/08* (2013.01); *C07D 209/14* (2013.01); *C07D 209/18* (2013.01); *C07D 209/20* (2013.01); *C07D 209/42* (2013.01); *C07D 209/60* (2013.01); *C07D 405/14* (2013.01); *C07D 409/14* (2013.01); *C07D 413/06* (2013.01); *C07D 417/06* (2013.01); *C09B 23/04* (2013.01); *C09B 23/06* (2013.01); *C09B 23/083* (2013.01); *C09B 45/20* (2013.01); *G02B 5/223* (2013.01)
USPC .......................... 359/885; 428/195.1; 548/455

(58) Field of Classification Search
CPC ..................................................... G11B 7/2472
USPC ................. 428/64.4, 64.8, 195.1; 430/270.2, 430/270.21; 548/518, 455; 359/885
See application file for complete search history.

(56) References Cited

U.S. PATENT DOCUMENTS

| | | | |
|---|---|---|---|
| 6,335,450 B1 | 1/2002 | Farooqui et al. | |
| 6,939,975 B2 | 9/2005 | Kawakami et al. | |
| 7,943,849 B2 * | 5/2011 | Tanabe et al. | 136/263 |
| 2004/0054192 A1 | 3/2004 | Kawakami et al. | |
| 2006/0051758 A1 * | 3/2006 | Mujumdar et al. | 435/6 |
| 2009/0054652 A1 | 2/2009 | Yano et al. | |
| 2009/0098410 A1 * | 4/2009 | Nishimoto et al. | 428/704 |
| 2009/0234122 A1 * | 9/2009 | Aizawa et al. | 546/6 |

FOREIGN PATENT DOCUMENTS

| | | |
|---|---|---|
| EP | 1 065 525 | 1/2001 |
| JP | 60-234892 | 11/1985 |
| JP | 5-173282 | 7/1993 |
| JP | 2001-301333 | 10/2001 |
| JP | 2003-057436 | 2/2003 |
| JP | 2004-045887 | 2/2004 |
| JP | 2004-174383 | 6/2004 |
| JP | 2005-059601 | 3/2005 |
| WO | 0212398 | 2/2002 |
| WO | 02/32860 | 4/2002 |
| WO | 2006/057113 | 6/2006 |
| WO | 2006/109618 | 10/2006 |
| WO | 2006/123786 | 11/2006 |
| WO | WO 2006123807 A1 * | 11/2006 |
| WO | 2007/114073 | 10/2007 |

OTHER PUBLICATIONS

International Search Report—PCT/JP2008/056036—Mar. 28, 2008.
European Search Report—EP 08 73 9160—Dec. 20, 2011.
International Search Report—PCT/JP2008/056036—Jun. 17, 2008.
Taiwanese Office Action dated May 6, 2013.

* cited by examiner

*Primary Examiner* — Gerard Higgins
(74) *Attorney, Agent, or Firm* — Young & Thompson

(57) ABSTRACT

Disclosed is a cyanine compound represented by general formula (I) below. Also disclosed are an optical filter using the compound and an optical recording material.

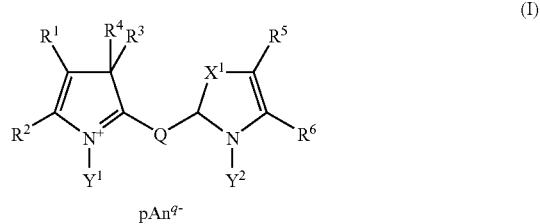

6 Claims, No Drawings

US 8,958,165 B2

CYANINE COMPOUND AND OPTICAL FILTER AND OPTICAL RECORDING MATERIAL CONTAINING SAME

TECHNICAL FIELD

This invention relates to a cyanine compound having an anchor group and an optical filter and an optical recording material containing the cyanine compound. The compound is useful as an optical element, particularly as a light absorber to be incorporated in an optical filter for an image display or an optical recording agent to be incorporated in an optical recording material used in an optical recording layer of an optical recording medium for writing and reading information using laser light.

BACKGROUND ART

Compounds having an intense absorption in a wavelength range of 450 to 1100 nm, especially those having an absorption peak wavelength ($\lambda_{max}$) between 480 nm and 620 nm, are used as an optical element in an optical recording layer of optical recording media including DVD-Rs, in an optical filter of image displays including liquid crystal displays (LCDs), plasma display panels (PDPs), electroluminescent displays (ELDs), cathode ray tube displays (CRTs), fluorescent display tubes, and field emission displays (FEDs), or in a CCD or CMOS image sensor.

The optical element of an image display is exemplified by a light absorber used in a color filter. An image display achieves a full color display using combinations of three primary colors of light, red, blue, and green. Light for displaying a color image contains a component that causes display quality reduction, such as light rays between green and red (550 to 600 nm) and a component that causes malfunction of an infrared remote controller (750 to 1100 nm). Then, an image display is equipped with an optical filter containing a light absorbing compound (light absorber) capable of selectively absorbing these unnecessary components of light.

A function to prevent reflection of ambient light, such as a fluorescent lamp, is also demanded in an optical filter. To prevent reflection of ambient light, an optical filter is required to absorb light with wavelengths of from 480 to 500 nm as well as the above-described unnecessary light components. Light in the recited wavelength range is near bright lines necessary to achieve image display. Accordingly, the light absorber to be used should have an especially narrow absorption band, i.e., a small half band width at $\lambda_{max}$. The light absorber is also required to withstand light and heat and continue to function.

Optical filters containing a light absorber that have been proposed to data include an optical filter containing a dipyromethene metal chelate compound having a maximum absorption wavelength of 440 to 510 nm (see Patent Document 1) and an optical filter containing a porphyrin compound having a maximum absorption wavelength of 440 to 510 nm (see Patent Document 2). These light absorbing compounds, however, are not good in view of their absorption wavelength characteristics or affinity for a solvent or a binder resin, and the optical filters containing them do not exhibit sufficient performance in a wavelength range of 480 to 500 nm.

Wavelengths of semiconductor lasers used in writing and reading information on the aforementioned optical recording media are in the ranges of 750 to 830 nm for CD-Rs and of 620 to 690 nm for DVD±Rs. In pursuit of a further increased capacity, optical discs using shorter wavelength lasers have been under study. For example, those using a write wavelength of 380 to 420 nm have been studied.

Various kinds of compounds are useful to form an optical recording layer of optical recording media for short wavelength lasers. For example, Patent Document 3 discloses a cyanine compound, Patent Document 4 reports a metal complex of a triazole compound, and Patent Document 5 reports a porphyrin compound. These compounds, however, are problematic for use as an optical recording material forming an optical recording layer in view of their poor affinity particularly to a metal reflective film and resistance to moist heat.

Patent Document 1: JP 2003-57436A
Patent Document 2: JP 2004-45887A
Patent Document 3: JP 2001-301333A
Patent Document 4: JP 2004-174838A
Patent Document 5: JP 2005-59601A

DISCLOSURE OF THE INVENTION

An object of the present invention is to provide a compound excellent in absorption wavelength characteristics and light resistance and is suited for use as an optical element, particularly in an optical filter for an image display device or in a laser optical recording material, and an optical filter and an optical recording material containing the compound.

As a result of intensive investigations, the present inventors have found that a cyanine compound having a specific structure exhibits high affinity for a metal reflective film and that use of the compound settles down the above problems.

Based on the above findings, the present invention has accomplished the object of the invention by providing a cyanine compound represented by general formula (I):

[Formula 1]

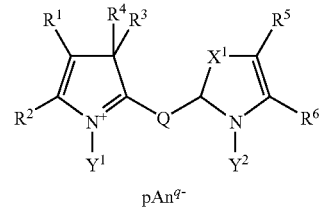

wherein $R^1$, $R^2$, $R^3$, $R^5$, and $R^6$ each independently represent a hydrogen atom, a hydroxyl group, an optionally substituted alkyl group having 1 to 10 carbon atoms, an optionally substituted alkoxy group having 1 to 10 carbon atoms, an optionally substituted aryl group having 6 to 30 carbon atoms, an optionally substituted arylalkyl group having 7 to 30 carbon atoms, a halogen atom, a nitro group, a cyano group, a substituent represented by general formula (II), (II'), or (III), or an anchor group; $R^4$ represents a substituent represented by general formula (II) or (II') or an anchor group; $R^1$ and $R^2$, and $R^5$ and $R^6$ may be taken together to form a cyclic structure optionally substituted with an anchor group; $X^1$ represents an oxygen atom, a sulfur atom, a selenium atom, —$CR^7R^8$—, —NH—, or —$NY^a$—; $R^7$ and $R^8$ in $X^1$ each independently represent an optionally substituted alkyl group having 1 to 10 carbon atoms, an optionally substituted aryl group having 6 to 30 carbon atoms, an optionally substituted arylalkyl group having 7 to 30 carbon atoms, a substituent represented by general formula (II), (II'), or (III), or an anchor group; $R^7$ and $R^8$ may be taken together to form a cyclic structure optionally substituted with an anchor group; $Y^1$ and $Y^2$, and $Y^a$ in $X^1$ each independently represent a hydrogen atom, an optionally substituted alkyl group having 1 to 10 carbon atoms, an optionally substituted alkoxy group having 1 to 10 carbon atoms, an optionally substituted aryl group having 6 to 30 carbon atoms, an optionally substituted arylalkyl group having 7 to 30 carbon atoms, a substituent represented by general formula (III), or an anchor group; -Q- represents a linking group comprising a polymethine chain optionally containing a cyclic structure and optionally substituted with an anchor group, the polymethine chain may have its hydrogen atom displaced by a halogen atom, a cyano group, a hydroxyl group, an alkyl group, an alkoxy group, or an aryl group, of which the alkyl, alkoxy or aryl group may further be substituted with the substituents recited; $An^{q-}$ represents a q-valent anion; q represents 1 or 2; and p represents a number necessary to neutralize an electric charge; with proviso that at least one of $R^1, R^2, R^3, R^4, R^5, R^6, R^7, Y^a, Y^1$, and $Y^2$ is an anchor group, or -Q- has an anchor group as a substituent, and the total number of anchor groups in the formula is 10 or smaller:

[Formula 2]

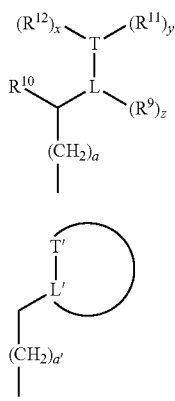

(II)

(II')

in general formula (II), the bond between L and T is a double bond, a conjugated double bond, or a triple bond; L represents a carbon atom; T represents a carbon atom, an oxygen atom, or a nitrogen atom; x, y, and z each independently represent 0 or 1, provided that, when T is oxygen, x=y=0, and, when T is nitrogen, y+z=0 or 1; a represents a number of 0 to 4; $R^9$ represents a hydrogen atom, a halogen atom, an alkyl group having 1 to 4 carbon atoms and optionally substituted with a halogen atom, or an alkoxy group having 1 to 4 carbon atoms and optionally substituted with a halogen atom; $R^{10}, R^{11}$, and $R^{12}$ each independently represent a hydrogen atom, a halogen atom, or an alkyl group having 1 to 4 carbon atoms and optionally substituted with a halogen atom; and $R^{10}$ and $R^{12}$ may be connected to each other to form a cyclic structure; in general formula (II'), the bond between L' and T' is a double bond or a conjugated double bond; L' represents a carbon atom; T' represents a carbon atom, an oxygen atom, or a nitrogen atom; a' represents a number of 0 to 4; the ring containing L' and T' is a 5-membered ring optionally containing a hetero atom, a 6-membered ring optionally containing a hetero atom, a naphthalene ring, a quinoline ring, an isoquinoline ring, an anthracene ring, or an anthraquinone ring; the ring containing L' and T' may be substituted with a halogen atom, a nitro group, a cyano group, an alkyl group, or an alkoxy group:

[Formula 3]

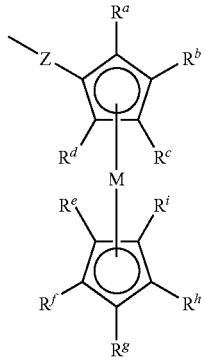

(III)

wherein $R^a, R^b, R^c, R^d, R^e, R^f, R^g, R^h$, and $R^i$ each independently represent a hydrogen atom or an alkyl group having 1 to 4 carbon atoms a methylene moiety of which may be displaced by —O— or —CO—; Z represents a single bond or an optionally substituted alkylene group having 1 to 8 carbon atoms a methylene moiety of which may be displaced by —O—, —S—, —CO—, —COO—, —OCO—, —SO$_2$—, —NH—, —CONH—, —NHCO—, —N=CH—, or —CH=CH—; and M represents Fe, Co, Ni, Ti, Cu, Zn, Zr, Cr, Mo, Os, Mn, Ru, Sn, Pd, Rh, Pt, or Ir.

The invention also provides an optical filter containing at least one cyanine compound represented by general formula (I) to achieve the object of the invention.

The invention also provides an optical recording material containing at least one cyanine compound represented by general formula (I) to achieve the object of the invention.

The invention also provides an optical recording medium including a substrate and an optical recording layer on the substrate, the optical recording layer being formed of the optical recording material to achieve the object of the invention.

BEST MODE FOR CARRYING OUT THE INVENTION

The cyanine compound of the invention and the optical filter and the optical recording material containing the cyanine compound will be described in detail with reference to their preferred embodiments.

The cyanine compound of the invention represented by general formula (I) is described first.

In general formula (I), the optionally substituted alkyl group of 1 to 10 carbon atoms as represented by $R^1, R^2, R^3, R^5, R^6, Y^1$, and $Y^2$ and $R^7, R^8$, and $Y^a$ in $X^1$ is exemplified by methyl, ethyl, propyl, isopropyl, butyl, sec-butyl, tert-butyl, isobutyl, amyl, isoamyl, tert-amyl, hexyl, cyclohexyl, cyclohexylmethyl, cyclohexylethyl, heptyl, isoheptyl, tert-heptyl, n-octyl, isooctyl, tert-octyl, 2-ethylhexyl, nonyl, isononyl, and decyl. Examples of the optionally substituted alkoxy group having 1 to 10 carbon atoms as represented by $R^1, R^2, R^3, R^5, R^6, Y^1$, and $Y^2$ and $Y^a$ in $X^1$ include methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, and 2-ethylhexyloxy. Examples of the optionally substituted aryl group having 6 to 30 carbon atoms as represented by $R^1, R^2, R^3, R^5, R^6, Y^1$, and $Y^2$ and $R^7, R^8$, and $Y^a$ in $X^1$ include phenyl, naphthyl, anthracen-1-yl, phenanthrene-1-yl, tetracenyl, pentacenyl, crysenyl, triphenylenyl, pyrenyl, picenyl, and perylenyl. Examples of the optionally substituted arylalkyl group as represented by $R^1$, $R^2$, $R^3$, $R^5$, $R^6$, $Y^1$, and $Y^2$ and $R^7$, $R^8$, and $Y^a$ in $X^1$ include benzyl, phenethyl, 2-phenylpropyl, diphenylmethyl, triphenylmethyl, styryl, and cinnamyl. Examples of the halogen atom as represented by $R^1$, $R^2$, $R^3$, $R^5$, and $R^6$ are fluorine, chlorine, bromine, and iodine.

Examples of the cyclic structure formed by the connection of $R^1$ and $R^2$, the connection of $R^5$ and $R^6$ and the connection of $R^7$ and $R^8$ in $X^1$ in general formula (I) include benzene, naphthalene, cyclohexane, cyclobutane, cyclopentane, cyclohexane, cycloheptane, piperidine, piperazine, pyrrolidine, morpholine, thiomorpholine, pyridine, pyrazine, pyrimidine, pyridazine, triazine, quinoline, isoquinoline, imidazole, oxazole, imidazolidine, pyrazolidine, isoxazolidine, and isothiazolidine. These rings may be fused with other ring(s) or may be substituted.

The linking group represented by -Q-, which comprises a polymethine chain which may contain a cyclic structure and may be substituted with an anchor group, is exemplified by polymethine chains having 1 to 7 carbon atoms. Particularly preferred of them are monomethine, trimethine, pentamethine, and heptamethine for their low production cost and absorption wavelength characteristics suitable to form an optical recording layer of an optical recording medium for short wavelength (380 to 420 nm) recording.

Preferred examples of the linking group as -Q- include groups (1) through (10) shown below.

[Formula 4]

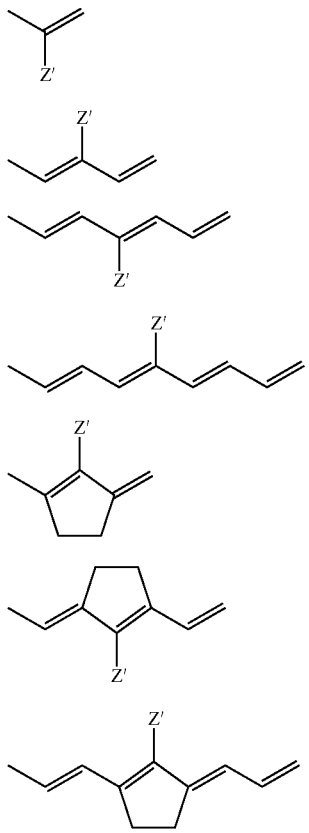

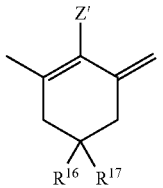

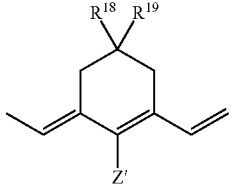

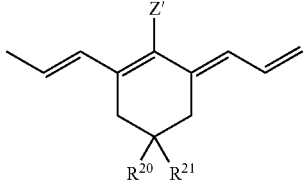

wherein $R^{16}$, $R^{17}$, $R^{18}$, $R^{19}$, $R^{20}$, and $R^{21}$ each independently represent a hydrogen atom, a hydroxyl group, a halogen atom, a cyano group, an aryl group having 6 to 30 carbon atoms, a diphenylamino group, an alkyl group having 1 to 10 carbon atoms, or an alkoxy group having 1 to 8 carbon atoms; and Z' represents a hydrogen atom, a hydroxyl group, a halogen atom, a cyano group, a diphenylamino group, an aryl group having 6 to 30 carbon atoms, an aralkyl group having 7 to 30 carbon group, or an alkyl group having 1 to 10 carbon atoms, the alkylene moiety of the alkyl or aralkyl group being optionally displaced by an ether linkage or a thioether linkage.

At least one of $R^1$, $R^2$, $R^3$, $R^4$, $R^5$, $R^6$, $R^7$, $R^8$, $Y^a$, $Y^1$, and $Y^2$ in general formula (I) is an anchor group, or -Q- has an anchor group as a substituent, provided that the total number of anchor groups is 10 or smaller. By the term "anchor group" is meant a group imparting to the cyanine compound chemical or electrostatic affinity or binding ability to a substrate containing it or a substrate with which it is contacted. Since a substrate is made of a metal or a resin, an anionic group is effective as an anchor group. Such an anchor group is preferably represented by general formula (VII):

[Formula 5-1]

$$L-P \qquad (VII)$$

wherein L represents a single bond or a divalent hydrocarbon group having 1 to 12 carbon atoms; and P represents an anionic group.

Examples of the divalent hydrocarbon group represented by L in general formula (VII) include an alkylene group having 1 to 8 carbon atoms, such as methylene, ethylene, propylene, or butylene; an arylene group having 6 to 12 carbon atoms, such as phenylene, tolylene, or naphthylene; an arylenealkylene group, such as phenylenemethylene or phenyleneethylene; and an arylenedialkylene group, such as phenylenedimethylene or phenylenediethylene. The methylene chain in the C1-C8 alkylene group, the arylenealkylene group, and the arylenedialkylene group may be displaced with —O—, —S—, —CO—, or —C≡C—. Examples of the anionic group represented by P include a carboxyl group, a sulfonic acid group, a phosphoric acid group, and a metal salt, ammonium salt, organoaluminum salt, or ester thereof. Of these anchor groups preferred are those represented by general formula (VIII) below for their low production cost and high affinity for a metallic reflective film, which is advantageous for use in an optical recording material. More preferred are those represented by general formula (IX) below.

[Formula 5-2]

$$-L-P'  \qquad (VIII)$$

wherein L represents a single bond or a divalent hydrocarbon group having 1 to 12 carbon atoms; and P' represents a carboxyl group, a sulfonic acid group, or a phosphoric acid group.

[Formula 5-3]

$$-L-COOH \qquad (IX)$$

wherein L represents a single bond or a divalent hydrocarbon group having 1 to 12 carbon atoms.

Examples of the anion represented by $An^{q-}$ which is monovalent in general formula (I) include inorganic anions, such as halide anions, e.g., chloride, bromide, iodide, and fluoride, perchlorate, chlorate, thiocyanate, hexafluorophosphate, hexafluoroantimonate, and tetrafluoroborate; organic sulfonate anions, such as benzenesulfonate, toluenesulfonate, trifluoromethanesulfonate, diphenylamine-4-sulfonate, 2-amino-4-methyl-5-chlorobenzenesulfonate, 2-amino-5-nitrobenzenesulfonate, and the sulfonates described in JP 8-253705A, JP 2004-503379A, JP 2005-336150A, and WO 2006/28006; organic phosphate anions, such as octylphosphate, dodecylphosphate, octadecylphosphate, phenylphosphate, nonylphenylphosphate, and 2,2'-methylenebis(4,6-di-t-butylphenyl)phosphonate; bistrifluoromethylsulfonylimide, bisperfluorobutanesulfonylimide, perfluoro-4-ethylcyclohexanesulfonate, tetrakis(pentafluorophenyl)borate, tetrakis(pentafluorophenyl)gallium, tris(fluoroalkylsulfonyl)carbanion, and dibenzoyltartrate. Examples of the anion represented by $An^{q-}$ which is divalent include a benzenedisulfonate anion and a naphthalenedisulfonate anion. If desired, a quencher anion capable of deexciting (quenching) an active molecule in an excited state, a metallocene compound anion of, for example, a ferrocene or a ruthenocene compound having an anionic group (e.g., a carboxyl group, a phosphonic acid group, or a sulfonic acid group) on its cyclopentadienyl ring can be used.

Examples of the quencher anion include anions represented by general formulae (A) and (B) shown below and formulae (C) and (D) shown below and those described in JP 60-234892A, JP 5-43814A, JP 5-305770A, JP 6-239028A, JP 9-309886A, JP 9-323478A, JP 10-45767A, JP 11-208118A, JP 2000-168237A, JP 2002-201373A, JP 2002-206061A, JP 2005-297407A, JP 7-96334B, and WO98/29257.

[Formula 6]

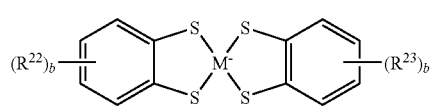

(A)

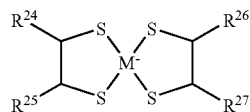

(B)

wherein M represents a nickel atom, a cobalt atom, or a copper atom, $R^{22}$ and $R^{23}$ each represent a halogen atom an alkyl group having 1 to 8 carbon atoms, an aryl group having 6 to 30 carbon atoms, or $-SO_2-G$; G represents an alkyl group, an aryl group, a halogen-substituted aryl group, a dialkylamino group, a diarylamino group, a piperidino group, or a morpholino group; a and b each independently represent an integer of 0 to 4; and $R^{24}$, $R^{25}$, $R^{26}$, and $R^{27}$ each independently represent an alkyl group, an alkylphenyl group, an alkoxyphenyl group, or a halogen-substituted phenyl group.

[Formula 7]

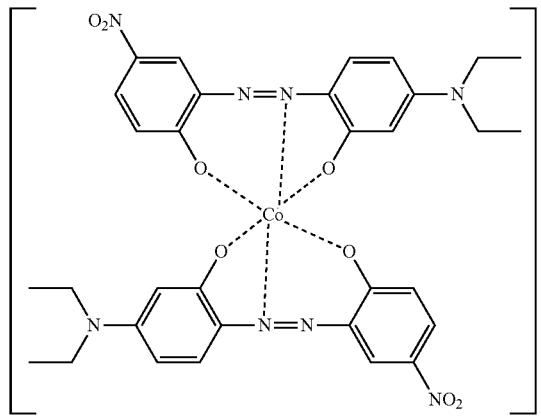

(C)

[Formula 8]

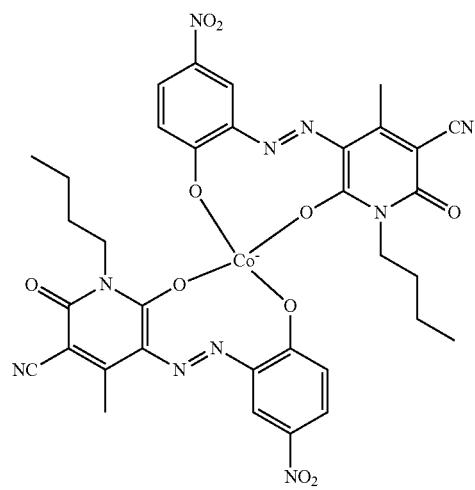

(D)

In general formula (II), examples of the halogen atom as represented by $R^9$, $R^{10}$, $R^{11}$, and $R^{12}$ include fluorine, chlorine, bromine, and iodine. Examples of the optionally halogen-substituted alkyl group having 1 to 4 carbon atoms as represented by $R^9$, $R^{10}$, $R^{11}$, and $R^{12}$ include methyl, ethyl, propyl, isopropyl, butyl, sec-butyl, tert-butyl, and isobutyl. Examples of the optionally halogen-substituted alkoxy group having 1 to 4 carbon atoms as represented by $R^9$ include methyloxy, ethyloxy, propyloxy, isopropyloxy, butyloxy, sec-butyloxy, tert-butyloxy, and isobutyloxy. Examples of the cyclic structure formed by the connection of $R^{10}$ and $R^{12}$ include the same examples as described with respect to the cyclic structure formed by the connection of $R^1$ and $R^2$, the connection of $R^5$ and $R^6$, and the connection of $R^7$ and $R^8$ in general formula (I).

In general formula (II'), the 5-membered ring that may contain a hetero atom is exemplified by a cyclopentene, a cyclopentadiene, an imidazole, a thiazole, a pyrazole, an oxazole, an isoxazole, a thiophene, a furan, and a pyrrole ring, and the 6-membered ring that may contain a hetero atom is exemplified by a benzene, a pyridine, a piperazine, a piperidine, a morpholine, a pyrazine, a pyrone, and a pyrrolidine ring.

In general formula (III), the alkyl group having 1 to 4 carbon atoms as represented by $R^a$, $R^b$, $R^c$, $R^d$, $R^e$, $R^f$, $R^g$, $R^h$, and $R^1$ include methyl, ethyl, propyl, isopropyl, butyl, sec-butyl, tert-butyl, and isobutyl. Examples of the alkyl group a methylene moiety of which is displaced by —O— include methoxy, ethoxy, propoxy, isopropoxy, methoxymethyl, ethoxymethyl, and 2-methoxyethyl. Examples of the alkyl group a methylene moiety of which is displaced by —CO— include acetyl, 1-carbonylethyl, acetylmethyl, 1-carbonylpropyl, 2-oxobutyl, 2-acetylethyl, and 1-carbonylisopropyl.

Examples of the optionally substituted alkylene group having 1 to 8 carbon atoms as represented by Z in general formula (III) include methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, and propane-2,2-diyl. Examples of the alkylene group whose methylene moiety is displaced by —O—, —S—, —CO—, —COO—, —OCO—, —$SO_2$—, —NH—, —CONH—, —NHCO—, —N=CH—, or —CH=CH— include methyleneoxy, ethyleneoxy, oxymethylene, thiomethylene, carbonylmethylene, carbonyloxymethylene, methylenecarbonyloxy, sulfonylmethylene, aminomethylene, acetylamino, ethylenecarboxyamide, ethaneimidoyl, ethenylene, and propenylene.

Examples of the substituent that may be possessed by the C1-C10 alkyl group as represented by $R^1$, $R^2$, $R^3$, $R^5$, $R^6$, $R^7$, $R^8$, $Y^a$, $Y^1$, and $Y^2$ the C1-C10 alkoxy group as represented by $R^1$, $R^2$, $R^3$, $R^5$, $R^6$, $Y^a$, $Y^1$, and $Y^2$, the C6-C30 aryl group as represented by $R^1$, $R^2$, $R^3$, $R^5$, $R^6$, $R^7$, $R^8$, $Y^a$, $Y^1$, and $Y^2$, and the C7-C30 arylalkyl group as represented by $R^1$, $R^2$, $R^3$, $R^5$, $R^6$, $R^7$, $R^8$, $Y^a$, $Y^1$, and $Y^2$ include the following groups and the above described anchor groups. In the cases where any of $R^1$, $R^2$, $R^3$, $R^5$, $R^6$, $Y^1$, and $Y^2$ and $R^7$, $R^8$, and $Y^a$ in $X^1$ is a carbon-containing group (for example, a C1-C10 alkyl group) having a carbon-containing substituent selected from the groups described below, the total number of carbon atoms of the carbon-containing group inclusive of the carbon atoms of the substituent should fall within the range recited. Examples of the substituent are: alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups such as methoxy, ethoxy, propoxy, isopropoxy, butoxy, sec-butoxy, tert-butoxy, isobutoxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy; alkylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctyltlio, tert-octylthio, and 2-ethylhexylthio; alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; aralkyl groups such as benzyl, phenethyl, diphenylmethyl, triphenylmethyl, styryl, and cinnamyl; aryl groups such as phenyl and naphthyl; aryloxy groups such as phenoxy and naphthoxy; arylthio groups such as phenylthio and naphthylthio; heterocyclic groups such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, and 2,4-dioxyoxazolidin-3-yl; halogen atoms such as fluorine, chlorine, bromine, and iodine; acyl groups such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups such as acetyloxy and benzoyloxy; an amino group; substituted amino groups such as ethylamino, dimethylamino, diethylamine, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; a sulfonamide group, a sulfonyl group, a carboxyl group, a cyano group, a sulfo group, a hydroxyl group, a nitro group, a mercapto group, an imide group, a carbamoyl group, and a sulfonamido group. These substituents may further be substituted. The carboxyl group and the sulfo group may form a salt.

Of the cyanine compounds of general formula (I) preferred are those represented by general formula (IV) below because of their low production cost, high affinity for a metallic reflective film, and absorption wavelength characteristics suited to form an optical recording layer of an optical recording medium using writing light with short wavelengths of 380 to 420 nm. Of the cyanine compounds represented by general formula (IV) more preferred are those represented by general formula (V) below because of their low production cost, high affinity for a metallic reflective film, and absorption wavelength characteristics suited to form an optical recording layer of an optical recording medium using writing light with short wavelengths of 380 to 420 nm.

Of the cyanine compounds of general formula (I) also preferred are those represented by general formula (VI)

below because of their low production cost, high affinity for a metallic reflective film, and absorption wavelength characteristics suited to form an optical recording layer of an optical recording medium using writing light with short wavelengths of 380 to 420 nm.

[Formula 9]

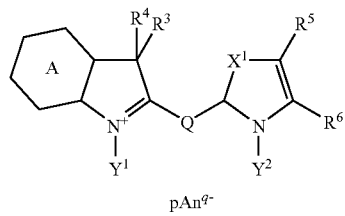

(IV)

wherein ring A represents an optionally substituted benzene ring or an optionally substituted naphthalene ring; $R^3$, $R^4$, $R^5$, $R^6$, $X^1$, $Y^1$, $Y^2$, -Q-, $An^{q-}$, p, and q are as defined for general formula (I).

[Formula 10]

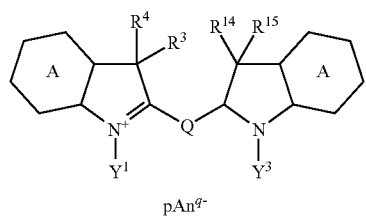

(V)

wherein ring A represents an optionally substituted benzene ring or an optionally substituted naphthalene ring; $R^3$, $R^4$, $Y^1$, -Q-, $An^{q-}$, p, and q are as defined for general formula (I); $R^{14}$ has the sane meaning as $R^3$; $R^{15}$ has the same meaning as $R^4$; and $Y^3$ has the same meaning as $Y^1$.

[Formula 11]

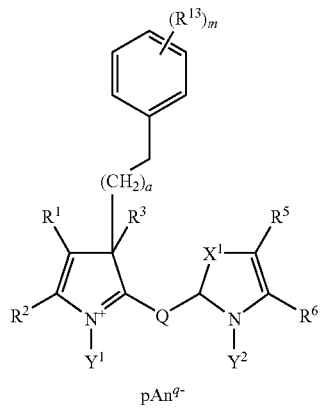

(VI)

wherein $R^1$, $R^2$, $R^3$, $R^5$, $R^6$, $X^1$, $Y^1$, $Y^2$, -Q-, $An^{q-}$, p, and q are as defined for general formula (I); a is as defined for general formula (II); $R^{13}$s, which may be the same or different, each represent a halogen atom, a nitro group, a cyano group, a carboxyl group, an alkyl group having 1 to 4 carbon atoms, or an alkoxy group having 1 to 4 carbon atoms; adjacent $R^{13}$s may be connected to each other to form a carbocyclic or heterocyclic ring having 3 to 12 carbon atoms; and m represents an integer of 0 to 5.

Examples of the substituent that may be possessed by the benzene or naphthalene ring as represented by ring A in general formulae (IV) and (V) include those recited above with respect to general formula (I).

Examples of the halogen atom as represented by $R^{13}$ in general formula (VI) include those recited above with respect to general formula (I). Examples of the C1-C4 alkyl group and the C1-C4 alkoxy group as represented by $R^{13}$ in general formula (VI) include those recited with respect to general formula (II). Examples of the C3-C12 carbocyclic ring formed by the connection of adjacent $R^{13}$s include cyclopropane, cyclobutane, cyclopentane, cyclohexane, cyclobutene, 3-methylcyclobutene, cyclopentene, cyclohexene, indene, and pentalene. Examples of the C3-C12 heterocyclic ring formed by the connection of adjacent $R^{13}$s include pyran, thiopyran, pyrazolyl, pyrrolidine, imidazolidine, pyrazolidine, thiazolidine, isothiazolidine, oxazolidine, isoxazolidine, piperidine, piperazine, piperidone, and morpholine.

Specific examples of the cyanine compound represented by general formula (I) include compound Nos. 1 through 52, whose structural formulae are illustrated below in which only cations are shown. The double bonds in the compounds of the invention may take on a resonant structure.

[Formula 12]

Compound No. 1

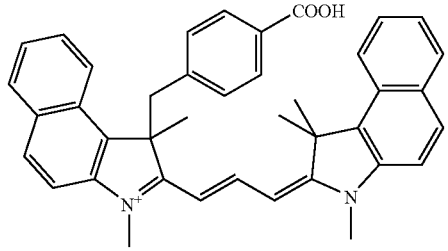

Compound No. 2

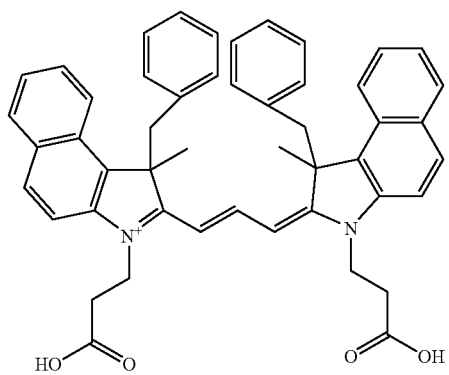

Compound No. 3
Compound No. 4
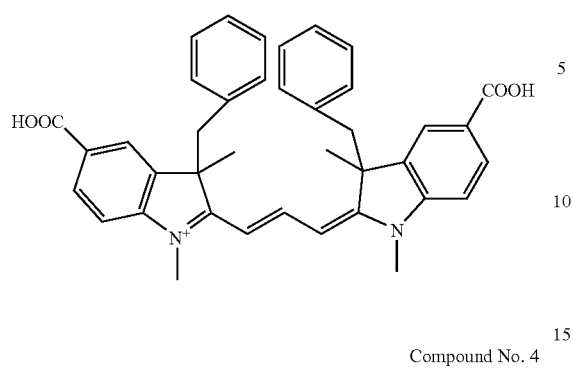
Compound No. 5
Compound No. 6
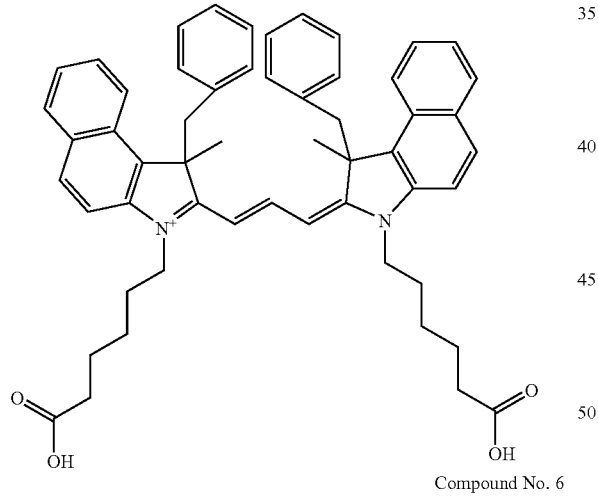
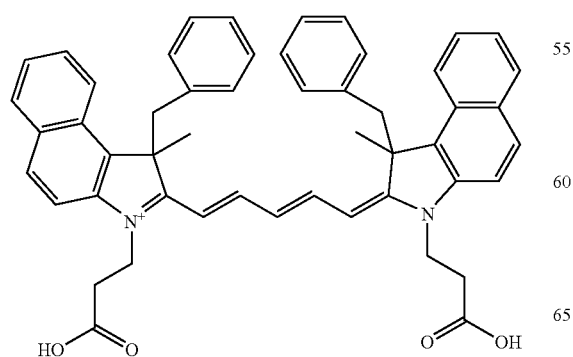
Compound No. 7
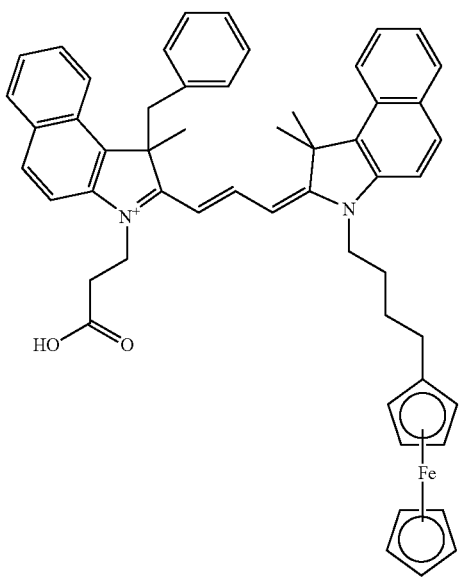
Compound No. 8
[Formula 13]
Compound No. 9
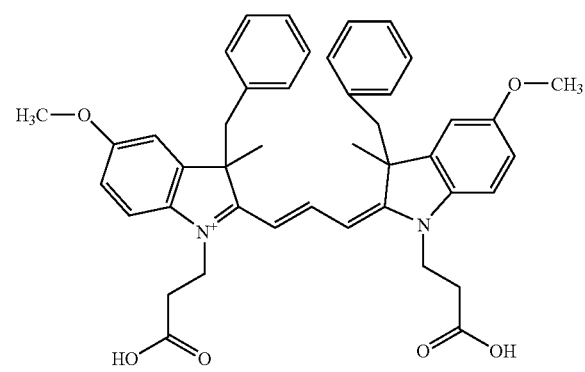

Compound No. 10
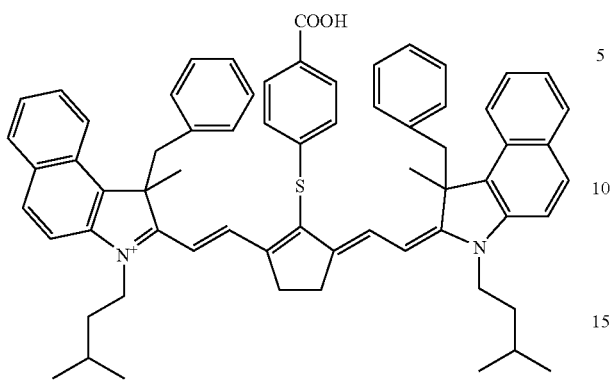
Compound No. 11
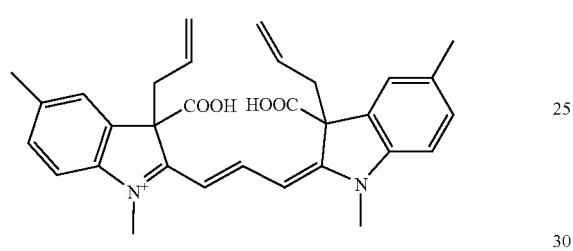
Compound No. 12
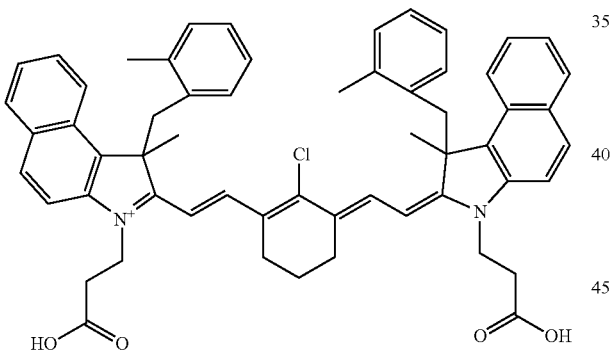
Compound No. 13
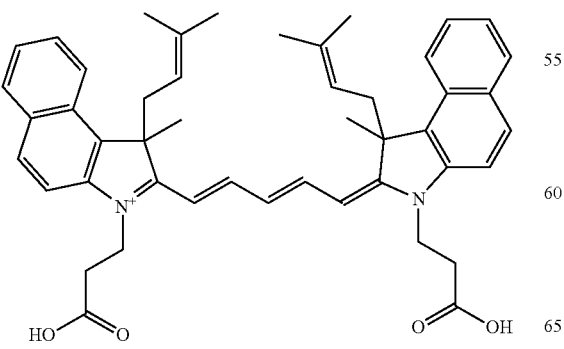
Compound No. 14
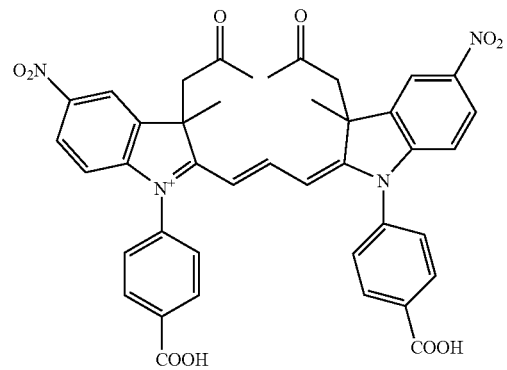
Compound No. 15
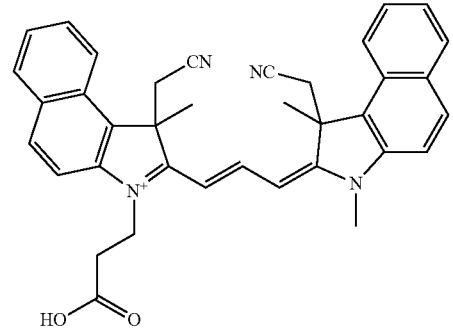
Compound No. 16
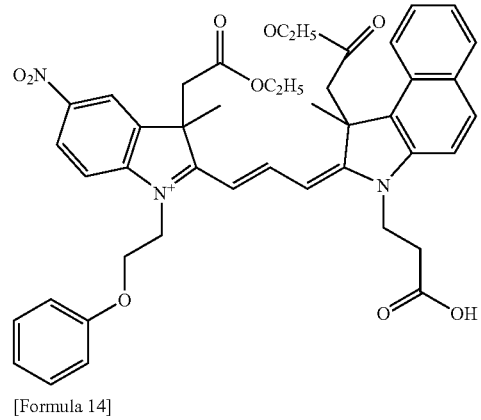
[Formula 14]
Compound No. 17
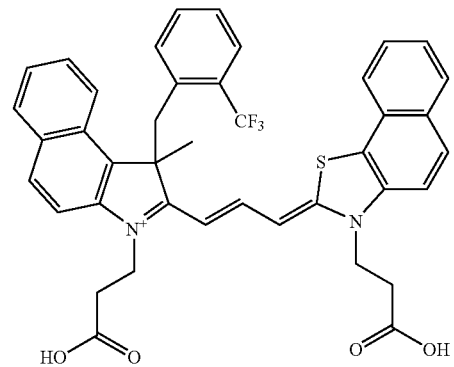

Compound No. 18
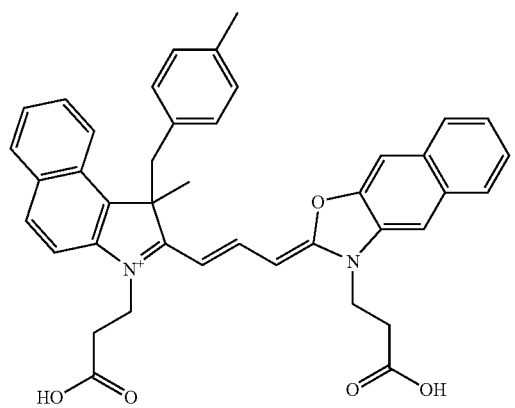
Compound No. 22
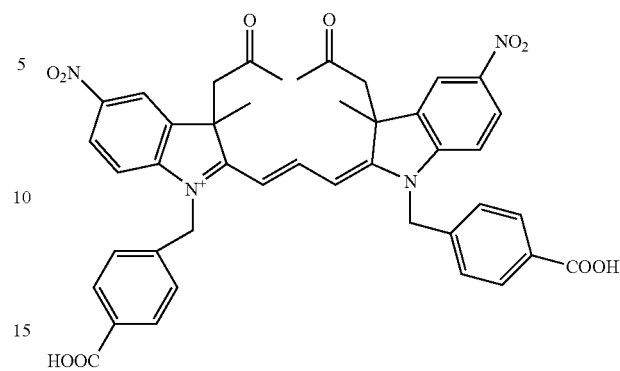
Compound No. 19
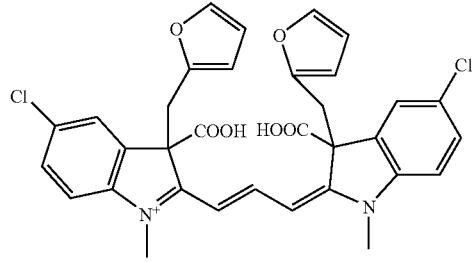
Compound No. 23
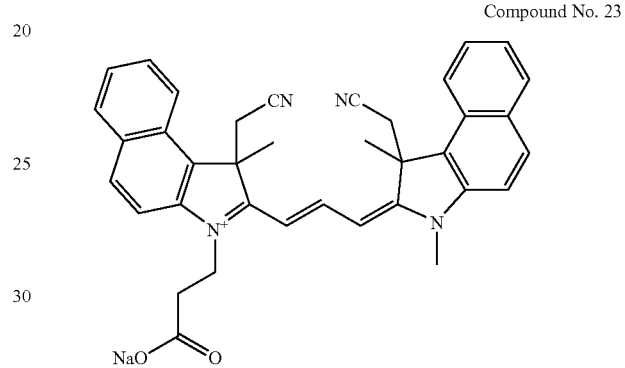
Compound No. 20
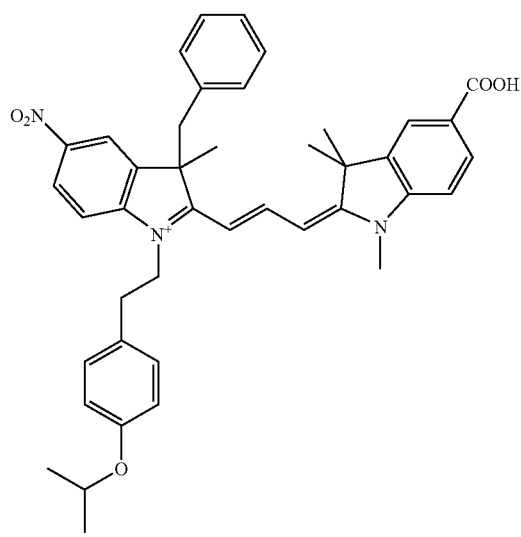
Compound No. 24
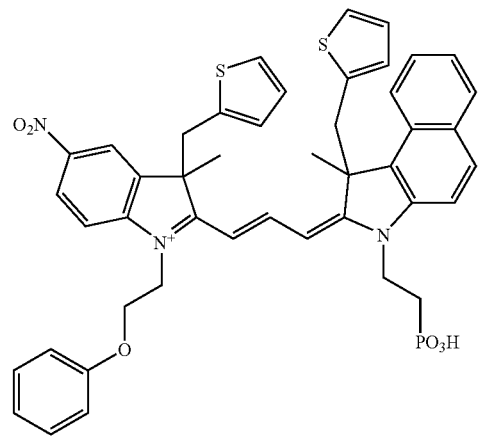
Compound No. 21
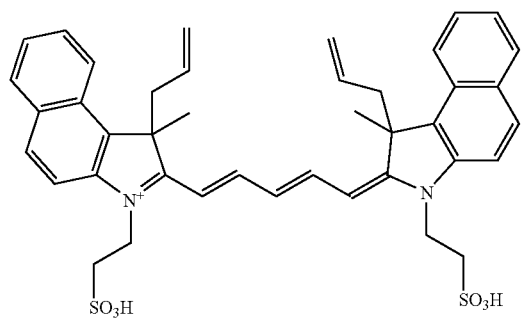
[Formula 15]
Compound No. 25

Compound No. 26
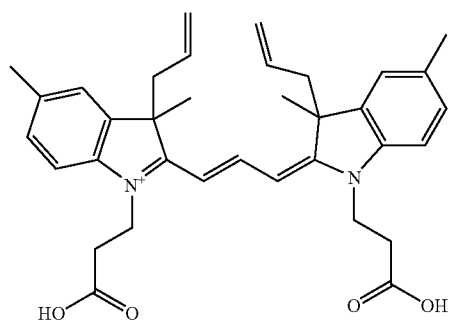
Compound No. 27
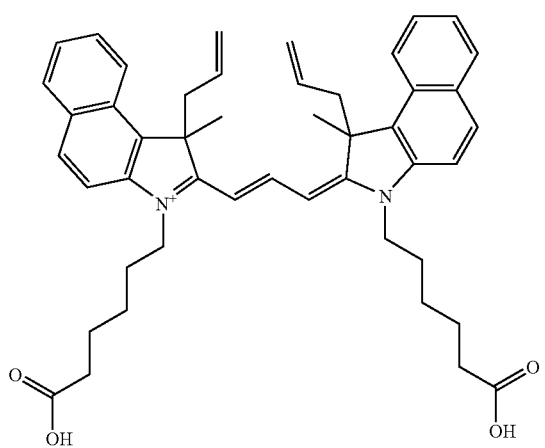
Compound No. 28
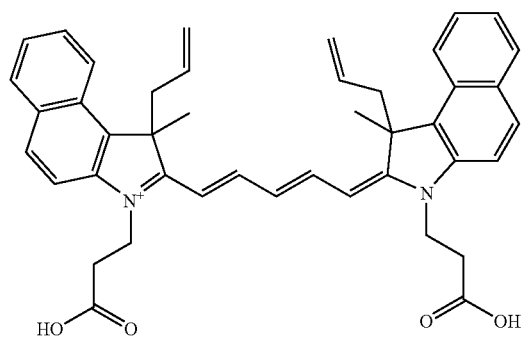
Compound No. 29
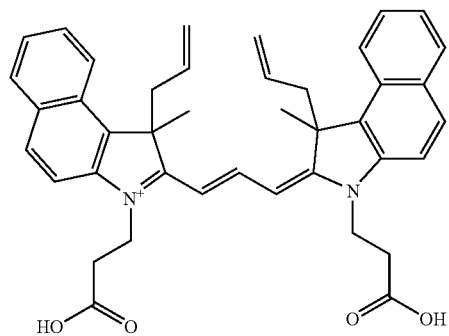
[Formula 16]
Compound No. 30
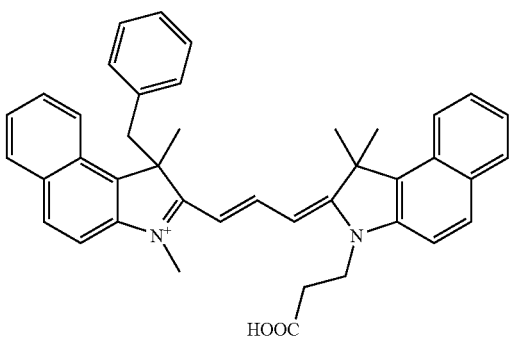
Compound No. 31
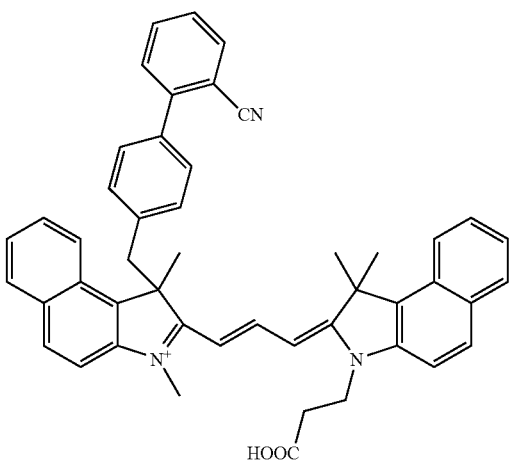
Compound No. 32
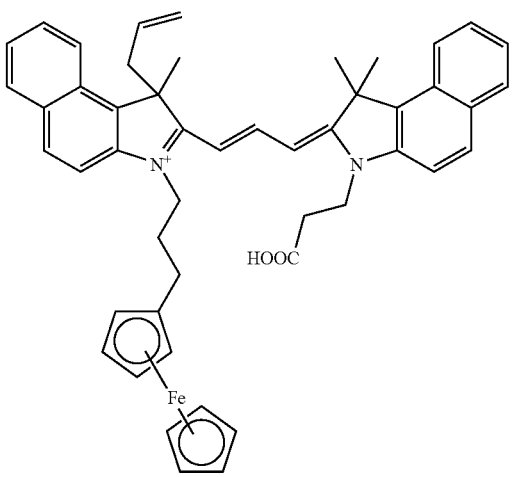
Compound No. 33
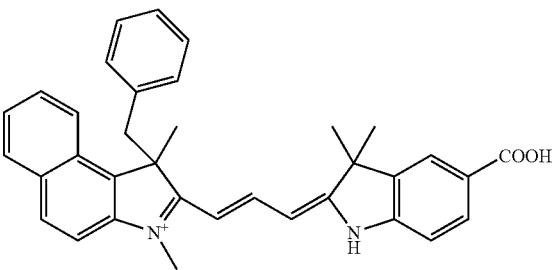

Compound No. 34
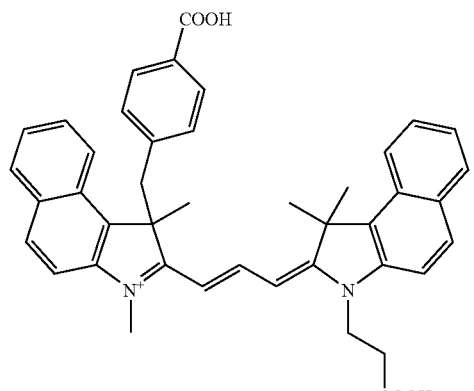
Compound No. 35
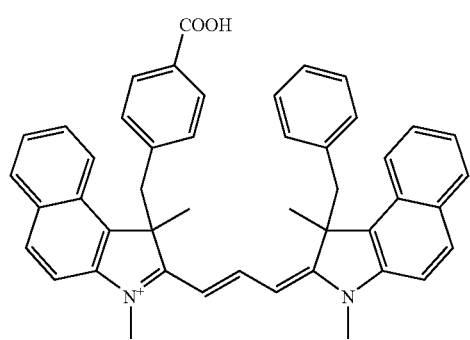
Compound No. 36
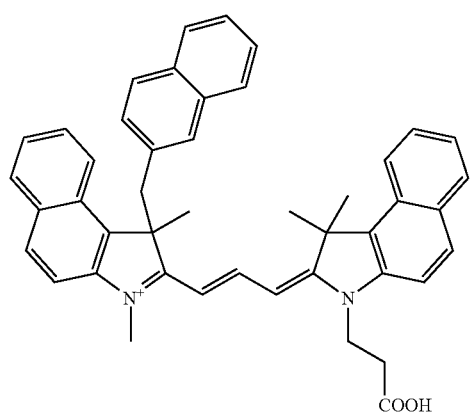
Compound No. 37
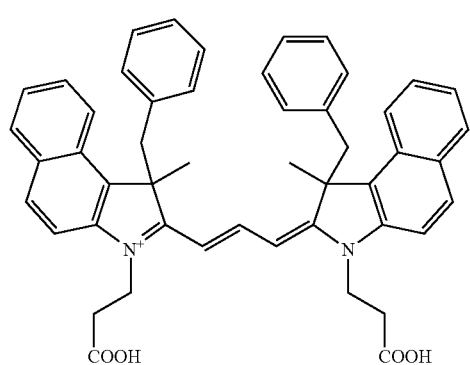
[Formula 17]
Compound No. 38
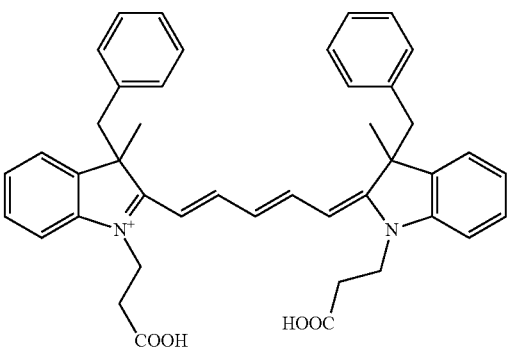
Compound No. 39
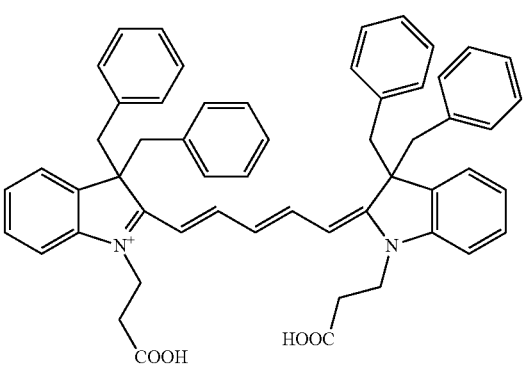
Compound No. 40
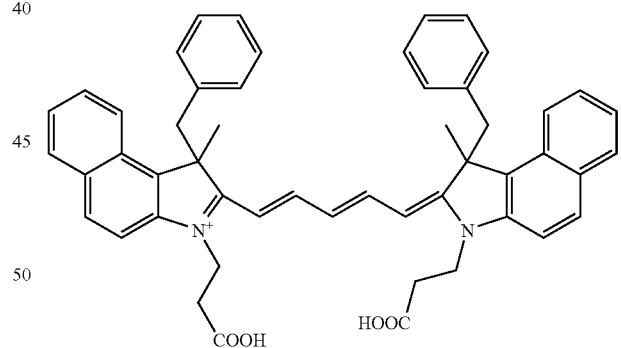
Compound No. 41
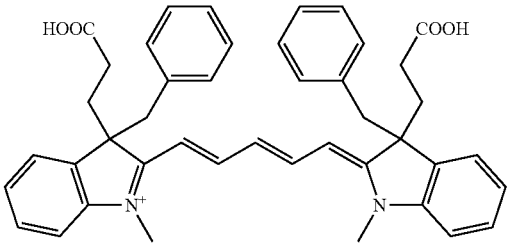

Compound No. 42
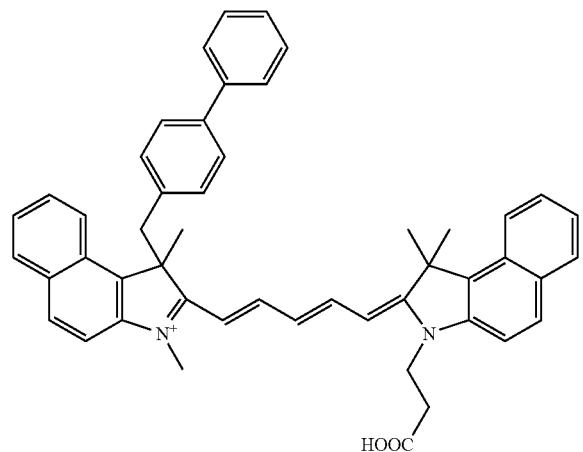
Compound No. 43
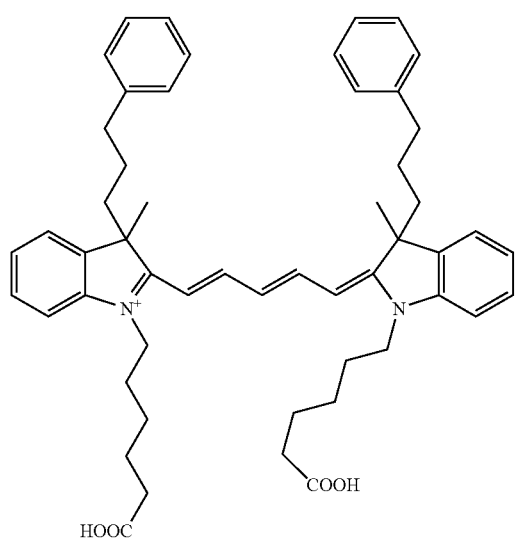
Compound No. 44
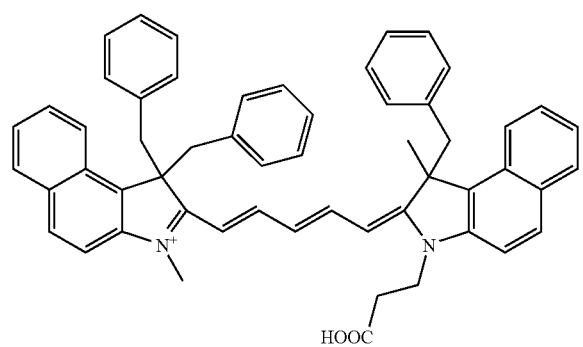
Compound No. 45
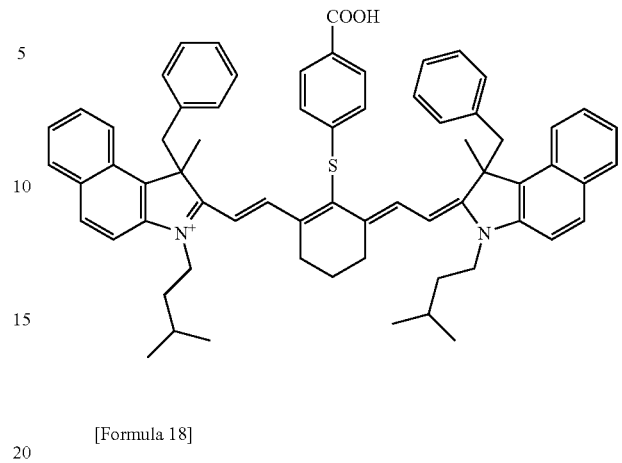
[Formula 18]
Compound No. 46
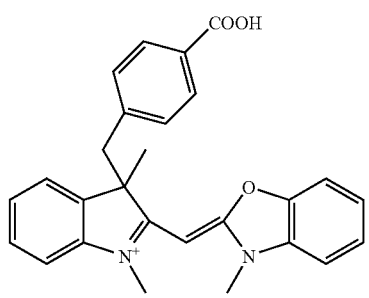
Compound No. 47
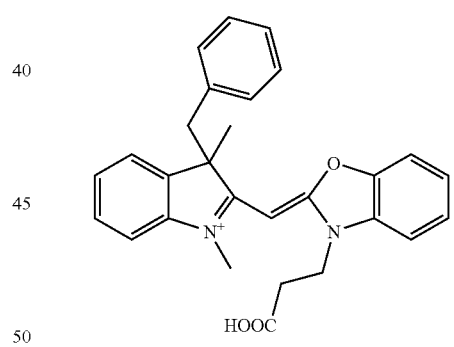
Compound No. 48
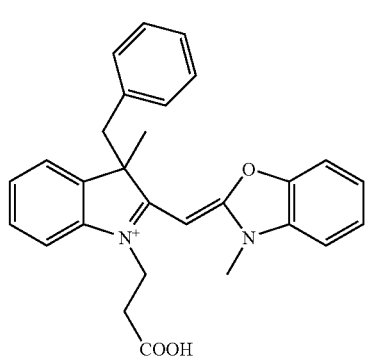

Compound No. 49

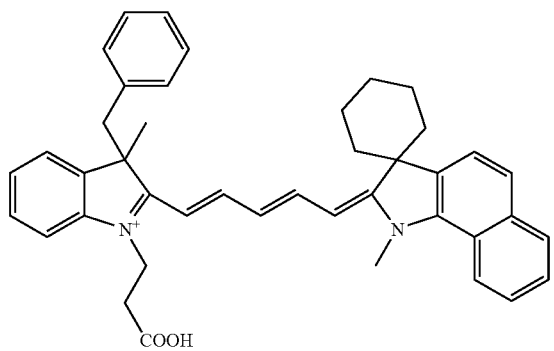

Compound No. 50

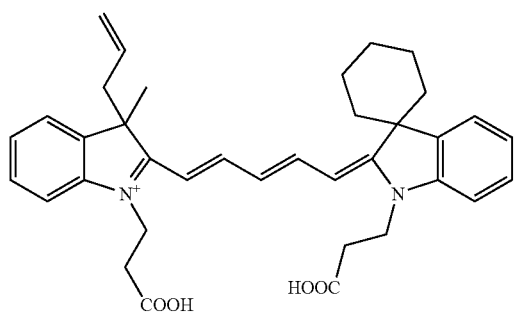

Compound No. 51

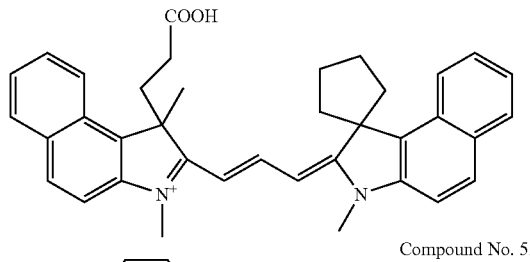

Compound No. 52

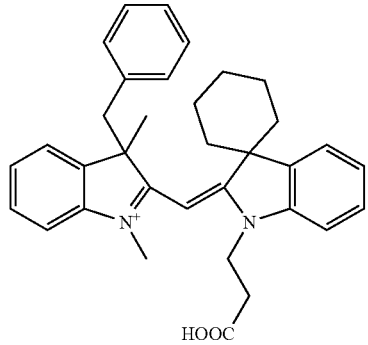

Some of the cyanine compounds of the invention represented by general formula (I) embrace optical isomers including enantiomers, diastereomers, and racemates thereof having a chiral center at the asymmetric atom to which $R^3$ and $R^4$ are bonded. Any of these optical isomers, individual or mixed, is usable.

The cyanine compounds of the invention represented by general formula (I) are not restricted by the process of preparation and can be obtained by well-known processes for synthesizing cyanine compounds. An anchor group can be introduced using well-known chemical reactions. For instance, a cyanine compound of the invention in which $Y^1$ and $Y^2$ in general formula (I) are each an anchor group is prepared in accordance with reaction scheme 1 below. That is, an indolenine compound and an alkyl halide having an anchor group are allowed to react to form a quaternary indolenine salt having the anchor group, which is then allowed to react with an amidine compound. The resulting product is further allowed to react with the quaternary indolenine salt having the anchor group.

A cyanine compound of the invention in which $R^3$, $R^4$, $R^7$, and $R^8$ are or contain an anchor group is prepared in accordance with reaction scheme 2 below. That is, a hydrazine compound and methyl ketone having an anchor group are allowed to cyclize to form an indolenine derivative with the anchor group, which is quaternized with an alkyl halide. The resulting quaternary intermediate is then allowed to react with an amidine compound.

Introducing an anchor group into -Q- is carried out by allowing an amidine compound having a halogen atom on -Q- and a quaternary indolenine salt to react with each other and allowing the product to react with a thiol compound having an anchor group in accordance with reaction scheme 3. A monomethine cyanine compound having an anchor group is prepared by allowing a quaternary indolenine salt and a quaternary salt having a thioether group at the 2-position to react with other as shown in reaction scheme 4. In reaction schemes below -Q'- represents a group providing a linking group Q, and -Q"- represents a group providing Q'.

Reaction scheme 1

[Formula 19-1]

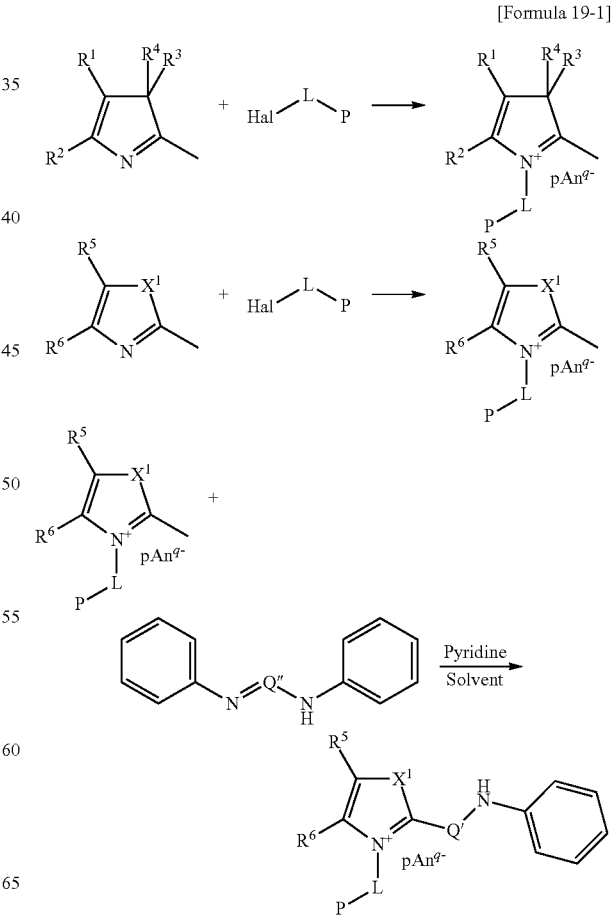

-continued
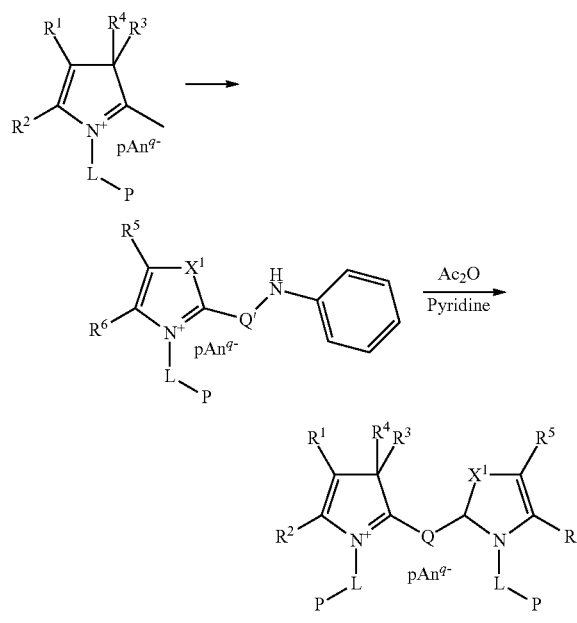
Reaction scheme 2
Reaction scheme 3
[Formula 20-1]
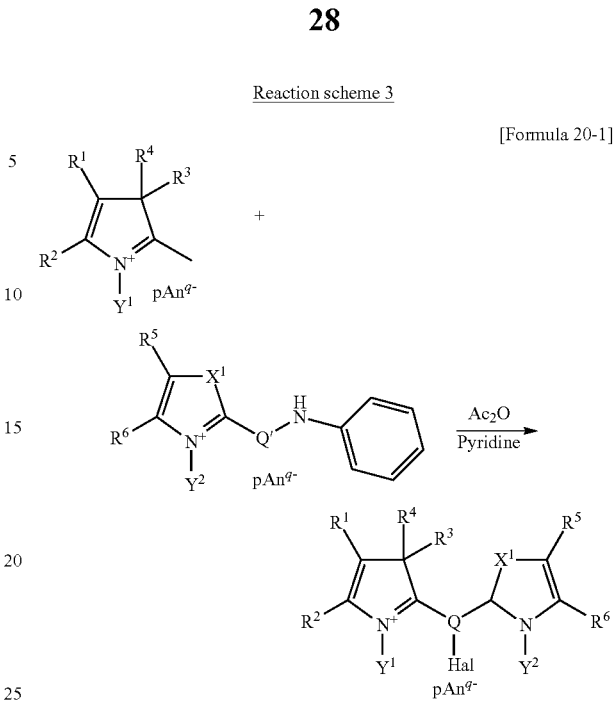
[Formula 19-2]
Reaction scheme 4
[Formula 20-2]
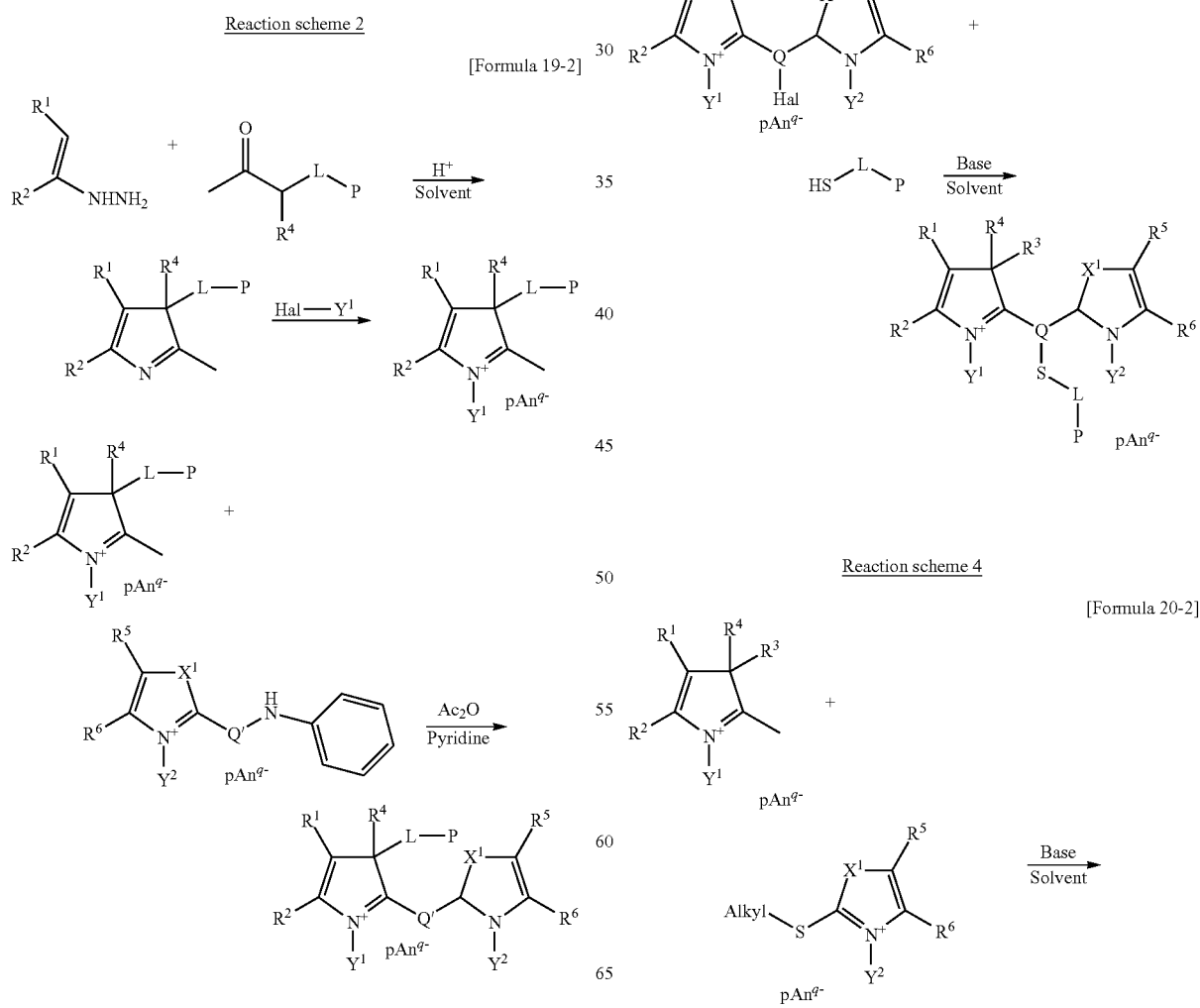

-continued

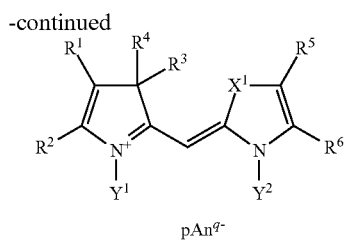

The cyanine compound of the invention is suitable as an optical element that absorbs light of 450 to 1100 nm, particularly light of 480 to 620 nm. The term "optical element" as used herein means an element that absorbs specific light to perform a function, including a light absorber, an optical recording agent, and a photosensitizer. For instance, a light absorber is used in an optical filter for an image display, and an optical recording agent is used in an optical recording layer of optical recording media, such as CD-Rs, DVD±Rs, HDDVD-Rs, and BD-Rs.

The optical filter of the present invention containing at least one cyanine compound of the invention will then be described.

When applied to an image display, the optical filter of the invention is usually disposed in front of a display device. The optical filter may be attached directly to the front surface of a display device or, where a front plate is provided in front of a display, it may be stuck to the front side or the back side of the front plate.

Examples of the image display include liquid crystal displays (LCDs), plasma display panels (PDPs), electroluminescence displays (ELDs), cathode ray tubes (CRTs), vacuum fluorescent displays, and field emission displays.

The cyanine compound of the invention is used in the optical filter, particularly for image displays, usually in an amount of 1 to 1000 mg/m$^2$, preferably 5 to 100 mg/m$^2$, per unit area of the optical filter. Amounts less than 1 mg/m$^2$ fail to produce sufficient effects of light absorption. Amounts exceeding 1000 mg/m$^2$ result in noticeable coloring of the filter, which can impair display quality or reduce the display brightness.

When applied to an image display, the optical filter of the invention may contain a light absorber other than the cyanine compound of the invention in order to adjust the color tone or a light absorber that absorbs light of wavelengths of 480 to 500 nm other than the cyanine compound of the invention in order to prevent reflection of ambient light. When applied to a plasma display, the optical filter may contain a near infrared absorber that absorbs light of 750 to 1100 nm other than the cyanine compound of the invention.

The light absorber for color tone adjustment is exemplified by those used to remove orange light of 550 to 600 nm, which include trimethine cyanine derivatives, such as trimethine indolium compounds, trimethine benzoxazolium compounds, and trimethine benzothiazolium compounds; pentamethine cyanine derivatives, such as pentamethine oxazolium compounds and pentamethine thiazolium compounds; squarylium dye derivatives, azomethine dye derivatives, xanthene dye derivatives, azo dye derivatives, pyromethene dye derivatives, azo metal complex derivatives, rhodamine dye derivatives, phthalocyanine derivatives, porphyrin derivatives, and dipyromethene metal chelate compounds.

Examples of the light absorber that absorbs light of 480 to 500 nm for preventing reflection of ambient light include trimethine cyanine derivatives, such as trimethine indolium compounds, trimethine oxazolium compounds, trimethine thiazolium compounds, and indolidene trimethine thiazonium compounds; phthalocyanine derivatives, naphthalocyanine derivatives, porphyrin derivatives, and dipyromethene metal chelate compounds.

Examples of the near infrared absorber that absorbs light of 750 to 1100 nm to prevent malfunction of an infrared remote controller include bisiminium derivatives; pentamethine cyanine derivatives, such as pentamethine benzoindolium compounds, pentamethine benzoxazolium compounds, and pentamethine benzothiazolium compounds; heptamethine cyanine derivatives, such as heptamethine indolium compounds, heptamethine benzoindolium compounds, heptamethine oxazolium compounds, heptamethine benzoxazolium compounds, heptamethine thiazolium compounds, and heptamethine benzothiazolium compounds; squarylium derivatives; nickel complexes, such as bis(stilbenedithiolato) compounds, bis(benzenedithiolato)nickel, compounds, and bis (camphordithiolato)nickel compounds; azo dye derivatives, phthalocyanine derivatives, porphyrin derivatives, and dipyromethene metal chelate compounds.

The optical filter of the invention may contain the light absorber for color tone adjustment, the light absorber for absorbing light of 480 to 500 nm, and the infrared absorber in the same layer that contains the cyanine compound of the invention or a separate layer. They are each used in an amount usually of 1 to 1000 mg/m$^2$, preferably of 5 to 100 mg/m$^2$, per unit area of the optical filter.

A typical structure of the optical filter of the present invention includes a transparent substrate, on which a primer layer, an antireflective layer, a hard coat layer, a lubricating layer, or a like layer is disposed as needed. The cyanine compound of the invention and the optional components, such as a color compound other than the cyanine compound of the invention and various stabilizers, are incorporated into the optical filter by (1) incorporating into the transparent substrate or any other layer or layers, (2) applying to the transparent substrate or any other layer or layers, (3) incorporating into a pressure-sensitive adhesive applied between adjacent two members selected from the transparent substrate and other layers, or (4) incorporating into an independently provided light absorbing layer. The cyanine compound of the invention is preferably incorporated into an adhesive applied between adjacent layers or an independently provided light absorbing layer.

The transparent substrate can be of inorganic materials, such as glass, or polymers including cellulose esters, such as diacetyl cellulose, triacetyl cellulose (TAC), propionyl cellulose, butyryl cellulose, acetylpropionyl cellulose, and nitrocellulose; polyamides; polyesters, such as polyethylene terephthalate, polyethylene naphthalate, polybutylene terephthalate, poly(1,4-cyclohexane dimethylene terephthalate), poly(ethylene-1,2-diphenoxyethane-4,4'-dicarboxylate), and polybutylene terephthalate; polystyrenes; polyolefins, such as polyethylene, polypropylene, and polymethylpentene; acrylic resins, such as polymethyl methacrylate; polycarbonates, polysulfones, polyether sulfones, polyether ketones, polyether imides, polyoxyethylene, and norbornene resins. It is preferred for the transparent substrate to have a transmittance of at least 80%, more preferably 86% or higher; a haze of riot more than 2%, more preferably 1% or less; and a refractive index of 1.45 to 1.70.

The transparent substrate may contain an infrared absorber, an ultraviolet absorber, an antioxidants (e.g., a phenolic or phosphorous-containing antioxidant), a flame retardant, a lubricant, an antistatic agent, inorganic fine particles, and the like. The transparent substrate may be subjected to various surface treatments.

Examples of the inorganic fine particles include silicon dioxide, titanium dioxide, barium sulfate, calcium carbonate, talc, and kaolin.

The surface treatments include chemical treatments, mechanical treatments, a corona discharge treatment, a flame treatment, a UV irradiation treatment, a radiofrequency treatment, a glow discharge treatment, an active plasma treatment, a laser treatment, a mixed acid treatment, and an ozone oxidation treatment.

The primer layer is a layer provided between the transparent substrate and a light absorbing layer containing a light absorber if provided. The primer layer is a layer containing a polymer having a glass transition temperature (Tg) of −60 to 60° C., a layer with a rough surface on the light absorbing layer side thereof, or a layer containing a polymer having affinity for the polymer of the light absorbing layer. Even where an independent light absorbing layer is not provided, a primer layer may be provided on the transparent substrate to improve the adhesion between the substrate and a layer provided thereon (e.g., an antireflective layer or a hard coat layer). A primer layer may also be provided in order to improve the affinity of the optical filter to an adhesive with which the optical filter is to be attached to an image display device. The thickness of the primer layer is suitably 2 nm to 20 µm, preferably 5 nm, to 5 µm, more preferably 20 nm to 2 µm, even more preferably 50 nm to 1 µm, most preferably 80 nm to 300 nm. The primer layer containing a polymer whose Tg ranges from −60 to 60° C. serves to bond the transparent substrate and a filter layer because of its tackiness. Examples of the polymer whose Tg is −60 to 60° C. include homo- and copolymers of vinyl chloride, vinylidene chloride, vinyl acetate, butadiene, neoprene, styrene, chloroprene, acrylic esters, methacrylic esters, acrylonitrile or methyl vinyl ether. The Tg of the polymer is preferably 50° C. or lower, more preferably 40° C. or lower, even more preferably 30° C. or lower, still even more preferably 25° C. or lower, most preferably 20° C. or lower. It is preferred for the primer layer to have an elastic modulus of 1 to 1000 MPa, more preferably 5 to 800 MPa, even more preferably 10 to 500 MPa, at 25° C. The primer layer with a rough surface serves for adhesion between the transparent substrate and a light absorbing layer provided on the rough surface side thereof. Such a primer layer can easily be formed by applying a polymer latex. The polymer latex preferably has an average particle size of 0.02 to 3 µm, more preferably 0.05 to 1 µm. Examples of the polymer having affinity for the binder polymer of the light absorbing layer include acrylic resins, cellulose derivatives, gelatin, casein, starch, polyvinyl alcohol, soluble nylon, and polymer latices. The optical filter may have two or more primer layers. The primer layer may contain a solvent for swelling a transparent substrate, a matting agent, a surfactant, an antistatic agent, a coating aid, a hardener, and so forth.

The antireflective layer essentially contains a low refractive sublayer having a lower refractive index than the transparent substrate. The refractive index of the low refractive sublayer is preferably 1.20 to 1.55, still preferably 1.30 to 1.50. The thickness of the low refractive sublayer is preferably 50 to 400 nm, still preferably 50 to 200 nm. The low refractive sublayer may be a layer of low-refractive, fluorine-containing polymer (see JP 57-34526A, JP 3-130103A, JP 6-115023A, JP 8-313702A, and JP 7-168004A), a layer formed by a sol-gel process (see JP 5-208811A, JP 6-299091A, and JP 7-168003A, or a layer containing fine particles (see JP 60-59250B, JP 5-13021A, JP 6-56478A, JP 7-92306A, and JP 9-288201A). The low refractive sublayer containing fine particles has microvoids formed between the fine particles or inside the fine particles. The low refractive sublayer containing fine particles preferably has a void of 3% to 50% by volume, still preferably 5% to 35% by volume.

In order to prevent reflection over a broad wavelength range, the antireflective layer preferably contains a medium and a high refractive sublayer in addition to the low refractive sublayer. The refractive index of a high refractive sublayer is preferably 1.65 to 2.40, still preferably 1.70 to 2.20. The refractive index of a medium refractive sublayer is set to be the intermediate between the refractive indices of the low and the high refractive sublayers and is preferably 1.50 to 1.90, still preferably 1.55 to 1.70. The thickness of the medium and the high refractive sublayers is preferably 5 nm to 100 µm, still preferably 10 nm to 10 µm, even still preferably 30 nm to 1 µm. The haze of the medium and the high refractive sublayers is preferably 5% or less, still preferably 3% or less, even still preferably 1% or less. The medium and the high refractive sublayers are formed by using polymer binders having relatively high refractive indices, such as polystyrene, styrene copolymers, polycarbonates, melamine resins, phenol resins, epoxy resins, and polyurethanes obtained by the reaction between a cyclic (alicyclic or aromatic) isocyanate and a polyol. Polymers having a cyclic (aromatic, heterocyclic or alicyclic) group and polymers having a halogen atom except fluorine as a substituent also have high refractive indices. Polymers prepared from monomers having a double bond introduced therein and thereby capable of radical polymerization are also useful.

Fine inorganic particles may be dispersed in the above recited polymer binders to increase the refractive index. Fine inorganic particles having a refractive index of 1.80 to 2.80 are used preferably. Such fine inorganic particles are preferably prepared from metal oxides or sulfides, such as titanium oxide (including rutile, rutile/anatase mixed crystals, anatase, and amorphous oxide), tin oxide, indium oxide, zinc oxide, zirconium oxide, and zinc sulfide. Preferred of them are titanium oxide, tin oxide, and indium oxide. The fine inorganic particles may contain the metal oxide or sulfide as a major component and other elements. The term "major component" means a component present in the particles at the highest weight percentage. Other elements that may be present include Ti, Zr, Sn, Sb, Cu, Fe, Mn, Pb, Cd, As, Cr, Hg, Zn, Al, Mg, Si, P, and S. The medium or high refractive sublayer can also be formed by using inorganic materials that are liquid per se or dispersible in a solvent and are capable of forming a film, such as alkoxides of various elements, salts of organic acids, coordination compounds having a coordinating compound bonded (e.g., chelate compounds), and inorganic active polymers.

The surface of the antireflective layer may be endowed with an antiglare function for scattering incident light thereby preventing the surrounding environment from reflecting on the antireflective layer. For example, fine roughness is formed on a transparent film, and an antireflective layer is formed on the roughened surface, or the surface of an antireflective layer is embossed with an embossing roll to have fine surface roughness. An antireflective layer with an antiglare function usually has a haze of 3% to 30%.

The hard coat layer has higher hardness than the transparent substrate. The hard coat layer preferably contains a crosslinked polymer. The hard coat layer can be formed using acrylic, urethane or epoxy polymers, oligomers or monomers, such as UV curing resins. The hard coat layer can also be made of a silica-based material.

A lubricating layer may be provided on the antireflective layer (low refractive sublayer). A lubricating layer imparts slip properties to the surface of the low refractive sublayer thereby improving scratch resistance. The lubricating layer can be formed using organopolysiloxanes (e.g., silicone oil), natural waxes, petroleum waxes, higher fatty acid metal salts, or fluorine-containing lubricants or derivatives thereof. The lubricating layer preferably has a thickness of 2 to 20 nm.

In the case when the cyanine compound of the invention is incorporated into a pressure sensitive adhesive applied between adjacent two members selected from the transparent substrate and other layers (method (3) supra), the compound of the invention and other components are added to a pressure sensitive adhesive, and adjacent two members selected from the transparent substrate and other layers are bonded with the resulting adhesive. Useful adhesives include transparent adhesives for laminated glass, such as silicone adhesives, urethane adhesives, acrylic adhesives, polyvinyl butyral adhesives, and ethylene-vinyl acetate adhesives. These adhesives may be used in combination with a metal chelate, isocyanate, epoxy, or like crosslinking agent as a curing agent. The thickness of the pressure sensitive adhesive layer is preferably 2 to 400 µm.

In the case when a light absorbing layer containing a light absorber, such as the cyanine compound of the invention, is provided independent of the other members (method (4) supra), the light absorbing layer can be formed of the cyanine compound of the invention either alone or as dispersed in a binder. Useful binders include naturally occurring polymers, such as gelatin, casein, starch, cellulose derivatives, and alginic acid, and synthetic polymers, such as polymethyl methacrylate, polyvinyl butyral, polyvinylpyrrolidone, polyvinyl alcohol, polyvinyl chloride, styrene-butadiene copolymers, polystyrene, polycarbonate, and polyamide.

The binder may be used together with an organic solvent. Various known solvents may be used as appropriate, including alcohols, such as isopropyl alcohol; ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; hydrocarbons, such as hexane, benzene, toluene, and xylene; and chlorinated hydrocarbons, such as methylene dichloride, dichloroethane, and chloroform. These organic solvents may be used either individually or as a mixture thereof.

The primer layer, antireflective layer, hard coat layer, lubricating layer, light absorbing layer, and the like can be formed by commonly employed coating methods including dip coating, air knife coating, curtain coating, roller coating, wire bar coating, gravure coating, and extrusion coating using a hopper (see U.S. Pat. No. 2,681,294). Two or more layers can be formed by simultaneous coating. For the details of simultaneous coating techniques, reference can be made in U.S. Pat. No. 2,761,791, U.S. Pat. No. 2,941,898, U.S. Pat. No. 3,508, 947, and U.S. Pat. No. 3,526,528, and Harasaki Yuji, *Coating Kogaku*, Asakura Shoten, p. 253 (1973).

Because the cyanine compound of the invention has a narrow half bandwidth of absorption, it shows small absorption of light necessary for display. Therefore, the optical filter containing the cyanine compound of the invention is especially suited for use in image displays for the purpose of improving display quality, the image displays including liquid crystal displays (LCDs), plasma display panels (PDPs), electroluminescence displays (ELDs), cathode ray tubes (CRTs), vacuum fluorescent displays, and field emission displays.

The optical filter of the invention is also useful in analysis equipment, fabrication of semiconductor devices, astronomical observation, optical communications, and so on.

The optical recording material of the present invention containing at least one cyanine compound of the invention will then be described. The optical recording material of the invention is used to make an optical recording layer of an optical recording medium. The optical recording medium comprises a substrate and the optical recording layer provided thereon. As used herein, the term "optical recording material" includes the cyanine compound of the invention per se and a mixture of the cyanine compound of the invention and an organic solvent hereinafter described and/or various compounds hereinafter described.

The method of forming an optical recording layer of an optical recording media using the optical recording material of the invention is not particularly limited. A wet coating technique is generally used, in which a solution of the cyanine compound of the invention and, if necessary various compounds described later in an organic solvent is applied to a substrate by spin coating, spray coating, dipping or a like method. Examples of the organic solvent include lower alcohols, such as methanol and ethanol, ether alcohols, such as methyl cellosolve, ethyl cellosolve, butyl cellosolve, and butyl diglycol; ketones, such as acetone, methyl ethyl ketone, methyl isobutyl ketone, cyclohexanone, and diacetone alcohol; esters, such as ethyl acetate, butyl acetate, and methoxyethyl acetate; acrylic esters, such as ethyl acrylate and butyl acrylate; fluoroalcohols, such as 2,2,3,3-tetrafluoropropanol; hydrocarbons, such as benzene, toluene, and xylene; and chlorinated hydrocarbons, such as methylene dichloride, dichloroethane, and chloroform. The amount of the organic solvent, when used, is preferably such that the content of the cyanine compound of the invention in the optical recording material of the invention may range from 0.1 to 10% by mass.

In the case where the optical recording medium of the invention is produced using the cyanine compound of the invention per se or a mixture of the cyanine compound of the invention and various compounds hereinafter described as an optical recording material of the invention, vacuum evaporation, sputtering or a like technique is employed to form the optical recording layer.

The optical recording layer is formed as a thin film with a thickness usually of 0.001 to 10 µm, preferably 0.01 to 5 µm.

The content of the cyanine compound of the invention in the optical recording material is preferably 10% to 100% by mass based on the solids content. The content of the cyanine compound of the invention in the optical recording layer is preferably 50% to 100% by mass. Accordingly, the optical recording material of the invention more preferably contains 50% to 100% by mass of the cyanine compound of the invention based on the solids content to give the above-recited preferred cyanine compound content in the optical recording layer.

The term "solids content of the optical recording material of the invention" refers to the total amount of components other than non-solid components including an organic solvent. The solids content of the optical recording material is preferably 0.01% to 100% by mass, more preferably 0.1% to 10% by mass.

Where necessary, the optical recording material of the invention may contain, in addition to the cyarline compound of the invention, compounds commonly employed in an optical recording layer, such as cyanine compounds other than those of the invention, azo compounds, phthalocyanine compounds, oxonol compounds, squarylium compounds, indole compounds, styryl compounds, porphin compounds, azulenium compounds, croconic methine compounds, pyrylium compounds, thiopyrylium compounds, triarylmethane compounds, diphenylmethane compounds, tetrahydrocholine compounds, indophenol compounds, anthraquinone compounds, naphthoquinone compounds, xanthene compounds, thiazine compounds, acridine compounds, oxazine compounds, spiropyran compounds, fluorene compounds, and rhodamine compounds. The optical recording material may further contain resins, such as polyethylene, polyester, polystyrene, and polycarbonate; surfactants, antistatic agents, lubricants, flame retardants, radical scavengers (e.g., hindered amines), pit formation accelerators (e.g., ferrocene derivatives), dispersants, antioxidants, crosslinking agents, light resistance imparting agents, and so forth. The optical recording material may furthermore contain an aromatic nitroso compound, an aluminum compound, an iminium compound, a bisiminium compound, a transition metal chelate compound, and the like as a quencher, e.g., for singlet oxygen. The content of these various compounds in the optical recording material is up to 50% by mass based on the solids content of the optical recording material.

The substrate on which the optical recording layer is provided may be of any material as long as it is substantially transparent to a write/read (recording/reproducing) light beam, including resins, such as polymethyl methacrylate, polyethylene terephthalate, and polycarbonate, and glass. The substrate may have any shape according to use, including a tape, a drum, a belt, and a disk.

A reflective layer of gold, silver, aluminum, copper, etc. may be formed on the optical recording layer by vacuum evaporation or sputtering. A protective layer may be formed using an organic material, such as an acrylic resin or a UV curing resin, or by sputtering using an inorganic material.

The optical recording material of the invention is suitable to form an optical recording layer of optical recording media on which information is written in the form of a thermal information pattern using a semiconductor laser, especially, known, high-speed single-layer, dual-layer, or multi-layer optical discs, such as CD-Rs, DVD±Rs, HD-DVD-Rs, and BD-Rs.

As described, the cyanine compound according to the invention is suitable as an optical element of an optical filter, an optical recording material, and the like and is also useful as a coloring agent in dye-sensitized solar cells, photoelectrochemical cells, nonlinear optical devices, electrochromic displays, holograms, organic semiconductors, organic ELs, silver halide light-sensitive materials, sensitizers, printing inks, inkjet inks, electrophotographic color toners, cosmetics, plastics, and so on; protein staining agents; luminescent dyes for detecting substances; and the like.

EXAMPLES

The present invention will now be illustrated in greater detail with reference to Preparation Example and Examples, but it should be understood that the invention is not construed as being limited thereto.

Example 1 describes preparation of the cyanine compound of the invention represented by general formula (I). Examples 2 to 5 describe fabrication of optical filters using the cyanine compound of Example 1. Example 6 shows preparation of the optical recording material of the invention using the cyanine compound of Example 1 and fabrication of an optical recording medium using the material. Comparative Example 1 shows an example of an optical recording material and an optical recording medium which use a compound structurally different from the cyanine compound of the invention. In Evaluation Example 1 and Comparative Evaluation Example 1, the cyanine compound of the invention of Example 1 and a comparative compound were evaluated for affinity for a metallic reflective film.

Examples 7 to 26 show preparation of the cyanine compounds of the invention. In Evaluation Example 2 and Comparative Evaluation Example 2, the cyanine compound obtained in Example 26 and a comparative compound were evaluated for affinity for a metallic reflective film. In Evaluation Examples 3 to 7 and Comparative Evaluation Examples 3 to 6, coating films of the cyanine compounds of the invention obtained in Examples 1, 15, 20, 16, and 24 and comparative compounds were evaluated for resistance to elution with water.

Example 1

Preparation of Compound No. 1 in Iodide Form

A nitrogen-purged reaction flask was charged with 1.14 g of a compound of [Formula 21] shown below, 1.18 g of N-methyl-3-methyl(4-carboxybenzyl)-2-methylbenzoindolenine iodide, 0.766 g of acetic anhydride, and 4.00 g of pyridine, and the mixture was stirred at 60° C. for 3 hours. To the reaction mixture were added 10 ml of chloroform and 20 ml of water to carry out oil/water separation. The solvent was removed by evaporation, and the residue was recrystallized from acetone to give 1.20 g (68%) of green powder, which was identified to be an iodide form of compound No. 1. The results of analyses for identification are shown below. The resulting compound was also analyzed by TG-DTA (in a 100 ml/min nitrogen stream, at a heating rate of 10° C./min) to determine the melting point and decomposition point. The endothermic peak temperature of the DTA curve was taken as a melting point, and the weight loss onset temperature in the TG curve was taken as a decomposition point. The same applies in the following Examples.

[Formula 21]

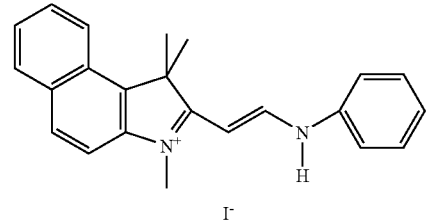

Results of Analyses:

[1] $^1$H-NMR (in DMSO-$d_6$) (chemical shift (ppm), multiplicity, number of protons of the peak top): (2.02, s, 6H), (2.17, s, 3H), (3.53, s, 3H), (3.66, d, 1H), (3.86, s, 3H), (4.22, d, 1H), 6.56-6.60, m, 4H), (7.45, d, 2H), (7.49-8.48, m, 12H), (8.69, t, 1H), (12.7, s, 1H)

[2] UV absorption (in chloroform): $\lambda_{max}$=591 nm; $\epsilon$=1.10×10$^5$

[3] Decomposition point (TG-DTA: 100 ml/min N$_2$, 10° C./min): 216.3° C. (peak top)

[4] Melting point: 211.7° C.

Example 2

Fabrication 1 of Optical Filter

A coating composition was prepared using the formulation below and applied to a 188 μm-thick polyethylene terephthalate (PET) film having been subjected to an adhesion enhancing treatment using a bar coater #9 and dried at 100° C. for 3 minutes to make an optical filter having a filter layer with a thickness of 10 μm on the PET film and containing 2.0 mg/m² of compound No. 1. The optical filter had a $\lambda_{max}$ of 591 nm with a half band width of 94.9 nm as measured with a UV-visible-near IR spectrophotometer V-570 (JASCO Corp.).
Formulation:

| | |
|---|---|
| Sumipex LG (acrylic resin binder, resin content: 40 mass %, from Sumitomo Chemical Co., Ltd.) | 2.5 g |
| Compound No. 1 in iodide form | 2 mg |
| Methyl ethyl ketone | 2.5 g |

Example 3

Fabrication 2 of Optical Filter

A pressure sensitive adhesive solution was prepared using the formulation shown below and applied to a 188 μm-thick PET film having been subjected to an adhesion enhancing treatment using a bar coater #30 and dried at 100° C. for 10 minutes to make an optical filter having an adhesive layer with a thickness of about 10 μm on the PET film and containing 2.0 mg/m² of compound No. 1. The optical filter had a $\lambda_{max}$ of 591.5 nm with a half band width of 95.0 nm as measured with a UV-visible-near IR spectrophotometer V-570 (JASCO Corp.).
Formulation:

| | |
|---|---|
| Compound No. 1 in iodide form | 2.0 mg |
| Acrylic pressure-sensitive adhesive DB Bond 5541 (from Daibond Industry Co., Ltd.) | 20 g |
| Methyl ethyl ketone | 80 g |

Example 4

Fabrication 3 of Optical Filter

A UV-curing varnish was prepared from the following formulation and applied to a 188 μm-thick PET film having been subjected to an adhesion enhancing treatment using a bar coater #9 and dried at 80° C. for 30 seconds. The coating film was irradiated with ultraviolet light from a high pressure mercury lamp equipped with an IR cut filter to make an optical filter with a cured filter layer having a thickness of about 5 μm and containing 2.0 mg/m² of compound No. 1. The optical filter had a $\lambda_{max}$ of 591 nm with a half band width of 94.8 nm as measured with a UV-visible-near IR spectrophotometer V-570 (JASCO Corp.).
Formulation

| | |
|---|---|
| Adekaoptomer KRX-571-65 (UV-curing resin, resin content: 80 mass %, from Adeka Corp.) | 100 g |
| Compound No. 1 in iodide form | 0.05 g |
| Methyl ethyl ketone | 60 g |

Example 5

Fabrication 4 of Optical Filter

A coating composition was prepared from the following formulation and applied to a 188 μm-thick PET film having been subjected to an adhesion enhancing treatment using a bar coater #9 and dried at 100° C. for 3 minutes to make an optical filter having a filter layer with a thickness of about 10 μm on the PET film and containing 2.0 mg/m² of compound No. 1. The optical filter had a $\lambda_{max}$ of 591 nm with a half band width of 95.0 nm as measured with a UV-visible-near IR spectrophotometer V-570 (JASCO Corp.).
Formulation:

| | |
|---|---|
| Polyester TP-220 (polyester resin from Nippon Synthetic Chemical Industry Co., Ltd.) | 100 g |
| Compound No. 1 in iodide form | 0.1 g |
| Methyl ethyl ketone | 60 g |

The optical filters of Examples 2 to 5 fabricated using the cyanine compound (I) of the invention show absorption in a specific wavelength range (550 to 620 nm) and, in particular, improve the color purity of red and are therefore apparently excellent in performance as an optical filter for image displays, especially PDPs.

Example 6

Compound No. 1 in iodide form obtained in Example 1 was dissolved in 2,2,3,3-tetrafluoropropanol in a concentration of 1.0% by mass to prepare a solution as an optical recording material. A titanium chelate compound T-50 (from Nippon Soda Co., Ltd.) was applied to a 12 cm diameter polycarbonate disk substrate, followed by hydrolysis to form a primer layer having a thickness of 0.01 μm. The 2,2,3,3-tetrafluoropropanol solution was applied onto the primer layer by spin coating to form an optical recording layer having a thickness of 100 nm. The resulting optical recording medium was designated optical recording medium No. 1.

Comparative Example 1

A comparative optical recording material was prepared in the same manner as in Example 6, except for replacing compound No. 1 in iodide form with comparative compound 0 shown below. A comparative optical recording medium was obtained using the resulting optical recording material in the same manner as in Example 6.

[Formula 22]

Comparative compound O

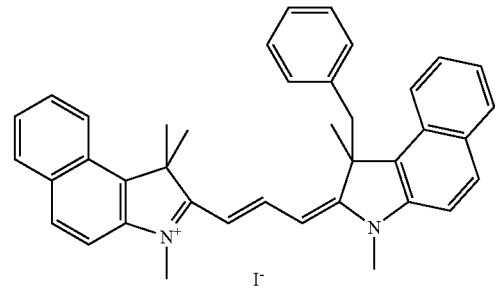

Evaluation Example 1 and Comparative Evaluation Example 1

Evaluation of Affinity for Metallic Reflective Film

A 10 μm-thick aluminum film was formed on a 200 μm-thick, 20 mm by 20 mm polycarbonate sheet by evaporation deposition. Compound No. 1 in iodide form (cyanine compound of the invention) was dissolved in 2,2,3,3-tetrafluoropropanol to prepare a 1 mass % solution. The solution was applied to the aluminum film of the polycarbonate sheet by spin coating at 2000 rpm for 60 seconds to prepare a specimen. Another specimen was prepared in the same manner, except for replacing compound No. 1 in iodide form with comparative compound 0. The resulting specimens were immersed in 80° C. water for 30 seconds. The reflectance (R) of the specimen was measured before and after the immersion at $\lambda_{max}$ of 635 nm, 650 nm, and 665 nm. The difference between the reflectance before the immersion ($R_1$) and that after the immersion ($R_2$) ($\Delta R=R_2-R_1$) was taken as a measure of affinity for a metallic reflective film. The results obtained are shown in Table 1.

TABLE 1

|  | 635 nm | 650 nm | 665 nm |
| --- | --- | --- | --- |
| Evaluation Example 1 | 1.2% | 1.4% | 0% |
| Comparative Evaluation Example 1 | 10.2% | 11.8% | 10.6% |

The results in Table 1 show that the metal reflective film having the cyanine compound of the invention thereon undergoes little change in reflectance on immersion in 80° C. water, proving highly water-resistant in contrast, the metal reflective film having the comparative compound thereon underwent a reflectance change of more than 10%, proving to have poor water resistance. This is considered to be because the cyanine compound of the invention has high affinity to a metallic reflective film owing to its anchor groups.

The cyanine compound of the invention exhibits high affinity to a metallic reflective film at wavelengths of 635 nm, 650 nm, and 665 nm, the laser wavelengths for DVD-Rs, and is therefore suited as an optical recording material.

Example 7

Preparation of Compound No. 30 in Hexafluorophosphate Form

A nitrogen-purged reaction flask was charged with 2.9 g of a compound of [Formula 23] shown below, 2.0 g of a compound of [Formula 24] shown below, 7.4 g of acetonitrile, and 0.8 g of triethylamine, followed by stirring at 45° C. for 4 hours. To the mixture were added 10 ml of chloroform and 20 ml of water to conduct oil/water separation. Subsequently, 20 ml of an aqueous solution containing 0.9 g of potassium hexafluorophosphate was added to effect salt exchange. The aqueous phase was discarded, and 20 ml of an aqueous solution containing 0.2 g of potassium hexafluorophosphate was again added to the organic phase to complete salt exchange. The oily phase was washed with two 15 ml portions of water. The solvent was removed by evaporation, and 1.2 g of acetone was added to dissolve the residue while heating. To the solution was added 12 g of butyl acetate for crystallization, followed by drying at 120° C. under reduced pressure to give 430 mg (12%) of green powder, which was identified to be compound No. 30 in hexafluorophosphate form. The results of analyses on the resulting green powder are shown below.

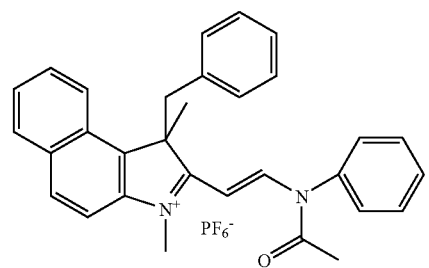

[Formula 23]

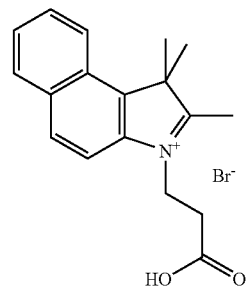

[Formula 24]

Results of Analyses:

[1] $^1$H-NMR (in DMSO-$d_6$) (chemical shift (ppm), multiplicity, number of protons of the peak top): (12.67, s, 1H), (8.73, t, 1H), (8.50, d, 1H), (8.29, d, 1H), (8.12-8.01, m, 4H), (7.83, d, 1H), (7.77, t, 1H), (7.68, t, 1H), (7.59-7.51, m, 3H), (6.96, t, 1H), (6.87, t, 2H), (6.66-6.61, m, 2H), (6.44, d, 2H), (4.51, t, 2H), (4.19, d, 1H), (3.61-3.50, m, 4H), (2.87, t, 2H), (2.16, s, 3H), (2.07-2.04, m, 6H)

[2] UV absorption (in methanol): $\lambda_{max}$=593.0 nm; $\epsilon$=1.14× $10^5$ M$^{-1}$cm$^{-1}$

[3] Decomposition point: 207° C.

Example 8

Preparation of Compound No. 31 in Perchlorate Form

In a nitrogen-purged reaction flask were put 2.9 g of a compound of [Formula 25] shown below, 0.9 g of acetic anhydride, and 9.3 g of acetonitrile, followed by stirring. To the mixture were further added 2.8 g of a compound of [Formula 26] shown below and 1.2 g of triethylamine, followed by stirring at 60° C. for 5 hours. To the reaction mixture were added 10 g of chloroform, 10 g of water, and 0.7 g of sodium perchlorate monohydrate to carry out oil/water separation. The solvent was removed by evaporation, and the residue was purified by silica gel column chromatography to give 130 mg (3%) of reddish purple powder, which was identified to be compound No. 31 in perchlorate form. The results of analyses on the resulting reddish purple powder are a shown below.

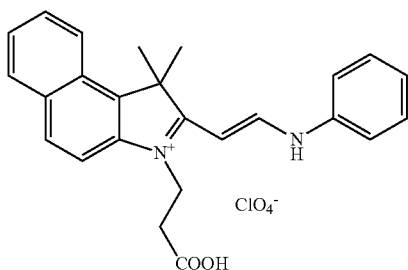

[Formula 25]

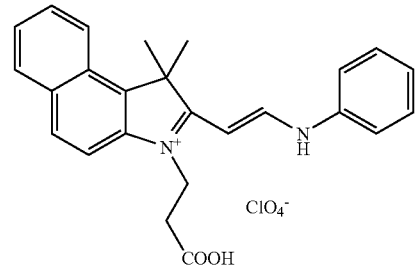

[Formula 27]

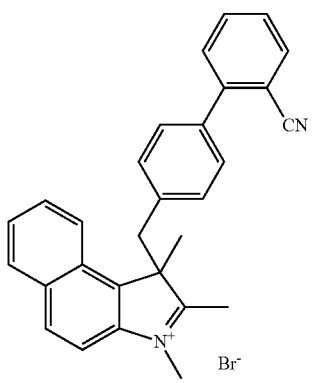

[Formula 26]

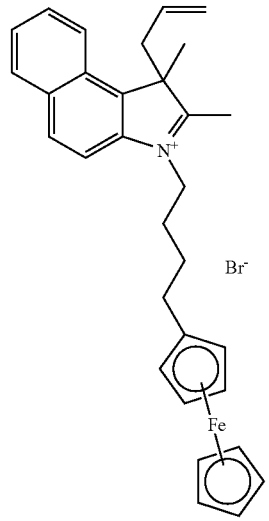

[Formula 28]

Results of Analyses:

[1] $^1$H-NMR (in DMSO-$d_6$) (chemical shift (ppm), multiplicity, number of protons of the peak top): (1.85, s, 3H), (2.02, s, 3H), (2.04, s, 3H), (2.44-2.49, m, 2H), (3.49, s, 3H), (3.65, d, 1H), (4.21, d, 1H), (4.44, t, 2H), (6.56, d, 2H), (6.58, d, 1H), (6.66, d, 1H), (7.08, d, 2H), (7.35, d, 1H), (7.45-7.56, m, 4H), (7.63-7.68, m, 2H), (7.37, t, 1H), 7.80-7.82, m, 2H), (8.00, d, 1H), (8.04-8.10, m, 3H), (8.26, d, 1H), (8.43, d, 1H), (8.71, t, 1H)

[2] UV absorption (in methanol). $\lambda_{max}$=593.5 nm; $\epsilon$=1.15× $10^5$ $M^{-1}cm^{-1}$

[3] Decomposition point: 137° C.

Example 9

Preparation of Compound No. 32 in Hexafluorophosphate Form

In a nitrogen-purged reaction flask were put 0.5 g of a compound of [Formula 27] shown below, 0.7 g of a compound of [Formula 28] shown below, 2.0 g of pyridine, and 0.1 g of acetic anhydride, followed by stirring at room temperature for 10 hours. Chloroform and water were added to the reaction mixture to conduct oil/water separation. Oil/water separation using an aqueous solution of potassium hexafluorophosphate was carried out, and the chloroform layer was washed with water. The solvent was removed by evaporation, and the residue was purified by silica gel thin layer chromatography to yield 0.1 g (10%) of purple powder, which was identified to be compound No. 32 in hexafluorophosphate form. The results of analyses on the resulting purple powder are shown below.

Results of Analyses:

[1] $^1$H-NMR (in DMSO-$d_6$) (chemical shift (ppm), multiplicity, number of protons of the peak top): (8.56, t, 1H), (8.28, t, 2H), (8.09-8.04, m, 4H), (7.79, d, 1H), (7.35, d, 1H), (7.66, t, 1H), (7.54-7.48, m, 2H), (6.61, q, 2H), (5.01-4.90, m, 1H), (4.76-4.67, m, 2H), (4.40, t, 2H), (4.27, t, 2H), (4.45-4.00, m, 9H), (3.66, dd, 1H), (3.11, dd, 1H), (2.36, br t, 4H), (2.03, s, 3H), (1.97, s, 6H), (1.85-1.75, m, 21H), (1.67-1.61, m, 2H)

[2] UV absorption (in methanol): $\lambda_{max}$=568.0 nm; $\epsilon$=9.22× $10^4$ $M^{-1}cm^{-1}$

[3] Decomposition point: 95° C.

Example 10

Preparation of Compound No. 33 in Hexafluorophosphate Form

In a nitrogen-purged reaction flask were put 2.7 g of a compound of [Formula 29] shown below, 1.9 g of a compound of [Formula 30] shown below, 6.6 g of pyridine, and 0.6 g of acetic anhydride, followed by stirring at 60° C. for 4 hours. Chloroform and water were added to the reaction mixture to conduct oil/water separation. The solvent was removed by evaporation, and the residue was purified by silica gel column chromatography and crystallization from chloroform to afford 0.5 g (15%) of brown powder, which was identified to be compound No. 33 in chloride hexafluorophosphate form. The results of analyses on the resulting brown powder are shown below.

[Formula 29]

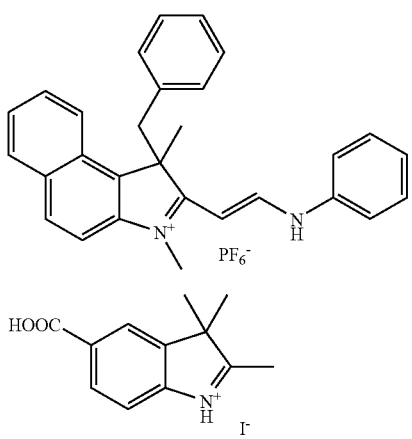

[Formula 30]

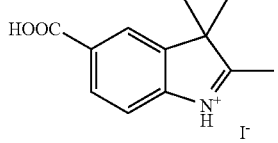

Results of Analyses:

[1] $^1$H-NMR (in DMSO-$d_6$) (chemical shift (ppm), multiplicity, number of protons of the peak top): (14.5, s, 1H), (12.6, s, 1H), (9.08, t, 1H), (8.44, d, 1H), (8.05, d, 2H), (7.97, t, 2H), (7.76, t, 1H), (7.56-7.50, m, 2H), (7.40, d, 1H), (6.91, m, 1H), (6.82, t, 2H), (6.48, d, 1H), (6.41, d, 2H), (6.21, d, 1H), (4.06, d, 1H), (3.98, d, 1H), (3.51, s, 3H), (2.15, s, 3H), (1.52, d, 6H)

[2] UV absorption (in methanol): $\lambda_{max}$=543.0 nm; $\epsilon$=4.50× $10^4$ M$^{-1}$cm$^{-1}$

[3] Decomposition point: 244° C.

Example 11

Preparation of Compound No. 34 in Perchlorate Form

In a nitrogen-purged reaction flask were put 2.42 g of a compound of [Formula 31] shown below, 2.1 g of a compound of [Formula 32] shown below, 7.3 g of acetonitrile, 0.8 g of triethylamine, and 0.8 g of acetic anhydride, followed by stirring at room temperature for 2.5 hours. To the reaction mixture were added 10 ml of chloroform and 20 ml of water to carry out oil/water separation. A solution of 150 mg of sodium perchlorate monohydrate in 20 ml of water was then added to carry out salt exchange. The oily layer was washed with two 20 ml portions of water. The solvent was removed by evaporation, and the residue was crystallized from 17.0 g of acetone. Drying at 120° C. under reduced pressure gave 1.3 g (36%) of brown powder, which was identified to be compound No. 34 in perchlorate form. The results of analyses on the resulting brown powder are shown below.

[Formula 32]

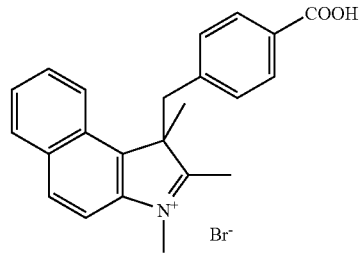

Results of Analyses:

1 $^1$H-NMR (in DMSO-$d_6$) (chemical shift (ppm), multiplicity, number of protons of the peak top): (8.66, t, 1H), (8.47, d, 1H), (8.26, d, 1H), (8.13-8.04, m, 3H), (7.96, d, 1H), (7.81, d, 1H), (7.74, t, 1H), (7.67, t, 1H), (7.57-7.48, m, 3H), (7.38, d, 2H), (6.66-6.56, m, 2H), (6.49, d, 2H), (4.48, t, 2H), (4.15, d, 1H), (3.62, d, 1H), (3.51, s, 3H), (2.75, t, 2H), (2.16, s, 3H), (2.03-2.01, m, 6H)

2. UV absorption (in methanol): $\lambda_{max}$=593.5 nm; $\epsilon$=1.14× $10^5$ M$^{-1}$cm$^{-1}$ 3 Decomposition point: 237° C.

Example 12

Preparation of Compound No. 35 in Hexafluorophosphate Form

In a nitrogen-purged reaction flask were put 1.2 g of a compound of [Formula 33] shown below, 1.1 g of a compound of [Formula 34] shown below, 3.2 g of acetonitrile, 0.3 g of acetic anhydride, and 0.3 g of triethylamine, followed by stirring at 40° C. for 3.5 hours. To the mixture were added 8 ml of chloroform and 15 ml of water to conduct oil/water separation. Subsequently, a solution of 0.5 g of potassium hexafluorophosphate in 20 ml of water was added to effect salt exchange. The aqueous phase was discarded, and a solution of 0.2 g of potassium hexafluorophosphate in 20 ml of water was added to the organic phase to complete salt exchange. The oily phase was washed with two 15 ml portions of water. The solvent was removed by evaporation, and 14.0 g of methyl isobutyl ketone was added for crystallization, followed by drying at 100° C. under reduced pressure to give 0.8 g (49%) of red powder, which was identified to be compound No. 35 in hexafluorophosphate form. The results of analyses on the resulting red powder are shown below.

[Formula 31]

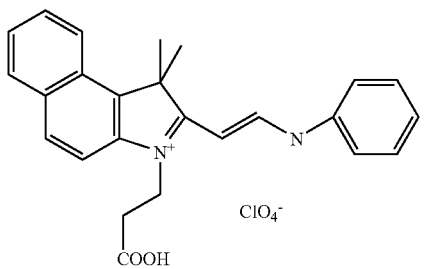

[Formula 33]

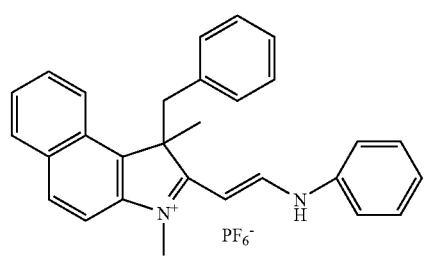

-continued

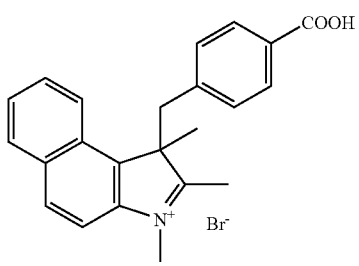

[Formula 34]

Results of Analyses:

[1] $^1$H-NMR (in DMSO-$d_6$) (chemical shift (ppm), multiplicity, number of protons of the peak top): (8.55, t, 1H), (8.51, d, 2H), (8.09-8.02, m, 4H), (7.77, t, 2H), (7.60-7.53, m, 4H), (7.39, t, 2H), (6.95, t, 1H), (6.89-6.86, m, 2H), (6.69-6.65, m, 2H), (6.56-6.45, m, 4H), (4.27-4.18, m, 2H), (3.76-3.69, m, 2H), (3.57, s, 6H), (2.21, s, 6H)

[2] UV absorption (in chloroform): $\lambda_{max}$=598.5 nm; $\epsilon$=1.04×10$^5$ M$^{-1}$cm$^{-1}$

[3] Decomposition point: 215° C.

[4] Melting point: 186° C.

Example 13

Preparation of Compound No. 36 in Perchlorate Form

In a nitrogen-purged reaction flask were put 1.9 g of a compound of [Formula 35] shown below, 1.7 g of a compound of [Formula 36] shown below, 11.9 g of acetonitrile, 0.6 g of triethylamine, and 0.6 g of acetic anhydride, followed by stirring at room temperature for 2 hours. To the reaction mixture were added 15 ml of chloroform and 20 ml of water to conduct oil/water separation. Subsequently, a solution of 0.2 g of sodium perchlorate monohydrate in 20 ml of water was added to carry out salt exchange. A solution of 0.3 g of sodium perchlorate monohydrate in 20 ml of water was further added to complete salt exchange. The oily layer was washed with two 20 ml portions of water. The solvent was removed by evaporation, and the residue was purified by column chromatography and dried at 120° C. under reduced pressure to yield 1.2 g (30%) of brown powder, which was identified to be compound No. 36 in perchlorate form. The results of analyses on the on the resulting brown powder are shown below.

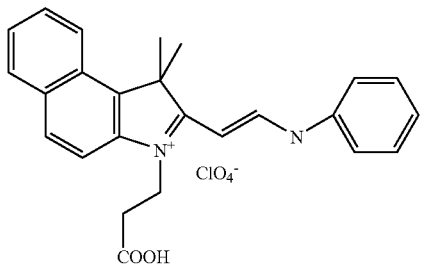

[Formula 35]

-continued

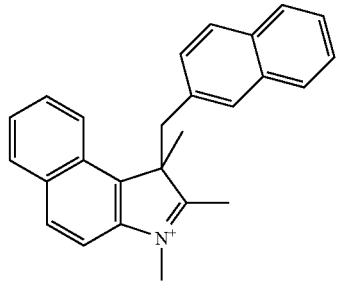

[Formula 36]

Results of Analyses:

[1] $^1$H-NMR (in DMSO-$d_6$) (chemical shift (ppm), multiplicity, number of protons of the peak top): (12.69, br, 1H), (8.76, t, 1H), (8.58, d, 1H), (8.30, d, 1H), (8.13-8.06, m, 3H), (7.98, d, 1H), (7.86-7.81, m, 2H), (7.68-7.42, m, 9H), (7.31, s, 1H), (6.70-6.64, m 2H), (6.55, d, 1H), (4.53, t, 2H), (4.36, d, 1H), (3.77, d, 1H), (3.50, s, 3H), (2.89, t, 2H), (2.20, s, 3H), (2.07-2.05, m, 6H)

[2] UV absorption (in methanol): $\lambda_{max}$=594.0 nm; $\epsilon$=0.93×10$^5$ M$^{-1}$cm$^{-1}$

[3] Decomposition point: 200° C.

Example 14

Preparation of Compound No. 37 in Iodide Form

A nitrogen-purged reaction flask was charged with 0.7 g of a compound of [Formula 37] shown below, 0.9 g of triethyl orthoformate, and 1.3 g of pyridine, followed by stirring at 50° C. for 4 hours. One gram, of water was added to the reaction system to precipitate solid, which was stirred under heat in a chloroform-acetone mixed solvent to yield 150 mg (23%) of purple powder. The purple powder was identified to be compound No. 37 in iodide form. The results of analyses on the resulting purple powder are shown below.

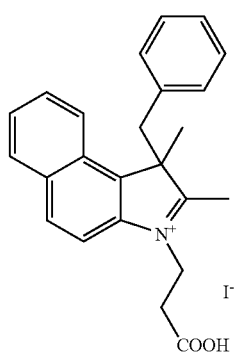

[Formula 37]

Results of Analyses:

[1] $^1$H-NMR (in DMSO-$d_6$) (chemical shift (ppm), multiplicity, number of protons of the peak top): (2.00-2.35, m, 10H), (3.60-3.70, m, 2H; 4.15-4.30, m, 6H), (6.39-6.48, m, 4H), (6.76-6.95, m, 8H; 7.55, t, 2H), (7.56, d, 2H), (7.77, t, 2H), (8.00, d, 2H), (8.07, d, 2H), (8.49, d, 2H), (8.87, t, 1H)

[2] UV absorption (in methanol): $\lambda_{max}$=602.0 nm; $\epsilon$=1.23× $10^5$ $M^{-1}cm^{-1}$

[3] Decomposition point: 197.9° C.

Example 15

Preparation of Compound No. 38 in Iodide Form

A nitrogen-purged reaction flask was charged with 1.3 g of a compound of [Formula 38] shown below, 1.5 g of 1,1,3,3-tetramethoxypropane, and 2.3 g of pyridine, followed by stirring at 100° C. for 8 hours. Chloroform and water were added to the reaction mixture to conduct oil/water separation. The solvent was removed by evaporation, and the residue was crystallized from acetone to afford 0.4 g (38%) of blue powder, which was identified to be compound No. 38 in iodide form. The results of analyses on the resulting blue powder are shown below.

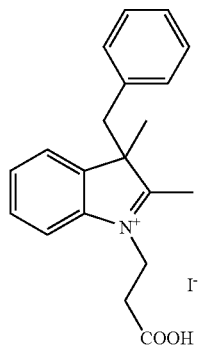

[Formula 38]

Results of Analyses:

[1] $^1$NMR (in DMSO-$d_6$) (chemical shift (ppm), multiplicity, number of protons of the peak top): (1.89, s, 6H), (1.91-1.95, m, 2H), (2.03-2.07, m, 2H), (3.50, d, 2H), (3.65, d, 2H), (3.95-4.05, m, 4H), (6.36, d, 2H), (6.53, d, 4H), (6.71, t, 1H), (6.94-7.01, m, 6H), (7.14, d, 2H), (7.24-7.33, m, 4H), (7.77, d, 2H), (8.55, t, 2H)

[2] UV absorption (in methanol): $\lambda_{max}$=654.0 nm; $\epsilon$=2.63× $10^5$ $M^{-1}cm^{-1}$

[3] Decomposition point: 192° C.

Example 16

Preparation of Compound No. 39 in Iodide Form

A nitrogen-purged reaction flask was charged with 1.5 g of a compound of [Formula 39] shown below, 1.5 g of 1,1,3,3-tetramethoxypropane, and 2.8 g of pyridine, followed by stirring at 100° C. for 8 hours. Chloroform and water were added to the reaction mixture to conduct oil/water separation. The solvent was removed by evaporation, and the residue was crystallized from acetone to afford 140 mg (10%) of black powder, which was identified to be compound No. 39 in iodide form. The results of analyses on the resulting black powder are shown below.

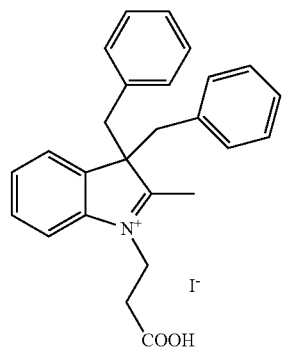

[Formula 39]

Results of Analyses:

[1] $^1$H-NMR (in DMSO-$d_6$) (chemical shift (ppm), multiplicity, number of protons of the peak top): (1.60-1.75, m, 4H), (3.77-3.95, m, 12H), (6.35, d) 2H), (6.68-6.76, m, 9H), (6.97-6.99, m, 14H), (7.26-7.33, m, 4H), (7.95, d, 2H), (8.79, t, 2H)

[2] UV absorption (in methanol): $\lambda_{max}$=664.5 nm; $\epsilon$=2.63× $10^5$ $M^{-1}cm^{-1}$

[3] Decomposition point: 210° C.

Example 17

Preparation of Compound No. 40 in Iodide Form

A nitrogen-purged reaction flask was charged with 1.7 g of a compound of [Formula 40] shown below, 2.6 g of tetramethoxypropane, and 3.4 g of pyridine, followed by stirring at 100° C. for 5 hours. Chloroform and an aqueous solution of sodium iodide were added to the reaction mixture to conduct oil/water separation. The solvent was removed by evaporation, and the residue was purified by silica gel column chromatography to give 190 mg (11%) of green powder, which was identified to be compound No. 40 in iodide form. The results of analyses on the resulting green powder are shown below.

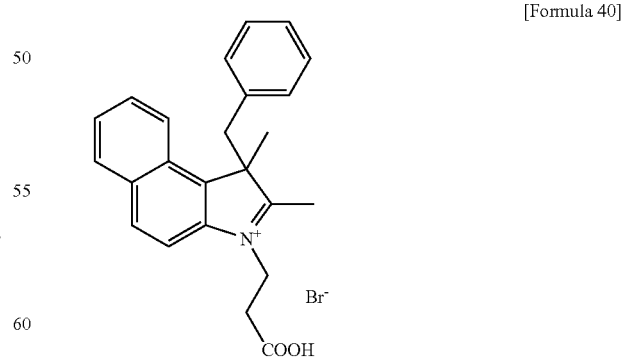

[Formula 40]

Results of Analyses:

[1] $^1$H-NMR (in DMSO-$d_6$) (chemical shift (ppm), multiplicity, number of protons of the peak top): (2.00-2.20, m, 4H), (2.13, s, 6H), (3.80-3.95, m, 2H), (4.01, d, 2H), (4.15-

4.22, m, 4H), (6.38-6.46, m, 6H), (6.75-6.93, m, 8H), (7.50, d, 2H), (7.55, t, 2H), (7.75, t, 2H), (8.00, d, 2H), (8.07, d, 2H), (8.48, d, 2H), (8.61, t, 1H)

[2] UV absorption (in methanol): $\lambda_{max}$=692.5 nm; $\epsilon$=1.65× 10 $M^{-1}cm^{-1}$

[3] Decomposition point: 175° C.

Example 18

Preparation of Compound No. 41 in Chloride Form

A nitrogen-purged reaction flask was charged with 1.2 g of a compound of [Formula 41] shown below, 0.5 g of tetramethoxypropane, and 3.4 g of pyridine, followed by stirring at 100° C. for 12 hours. Ten grams of chloroform and 10 ml of water were added to the reaction mixture to conduct oil/water separation, and the chloroform layer was washed with water. The crystals precipitated in the chloroform layer were collected by filtration to give 120 mg (12%) of purple powder, which was identified to be compound No. 41 in chloride form. The results of analyses on the resulting purple powder are shown below.

[Formula 41]

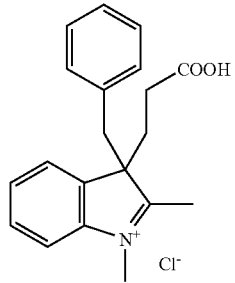

Results of Analyses:

[1] $^1$H-NMR (in DMSO-$d_6$) (chemical shift (ppm), multiplicity, number of protons of the peak top): (12.12, br, 2H), (8.53, t, 2H), (7.76, d, 2H), (7.38, t, 2H), (7.30, t, 2H), (7.19, d, 2H), (7.05-6.97, m, 6H), (6.67-6.62, m, 5H), (6.35, d, 2H), (3.74, d, 2H), (3.62, d, 2H), (3.35, s, 6H), (2.85-2.75, m, 2H), (2.68-2.63, m, 2H), (1.91-1.79, m, 2H), (1.47-1.41, m, 2H)

[2] UV absorption (in methanol): $\lambda_{max}$=652.5 nm; $\epsilon$=2.32× $10^5 M^{-1}cm^{-1}$

[3] Decomposition point: 208° C.

Example 19

Preparation of Compound No. 42 in Iodide Form

A nitrogen-purged reaction flask was charged with 1.2 g of a compound of [Formula 42] shown below, 0.2 g of acetic anhydride, and 6.5 g of pyridine, followed by stirring at room temperature for 1 hour. Subsequently, a compound of [Formula 43] shown below was added, followed by stirring at 80° C. for 6 hours. The solvent was removed by evaporation, and the residue was purified by silica gel column chromatography to give 250 mg (15%) of purple powder, which was identified to be compound No. 42 in iodide form. The results of analyses on the on the resulting purple powder are shown below.

[Formula 42]

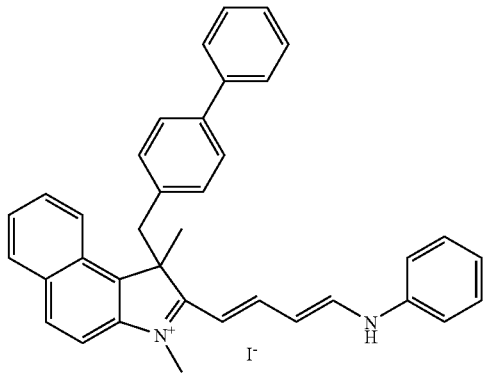

[Formula 43]

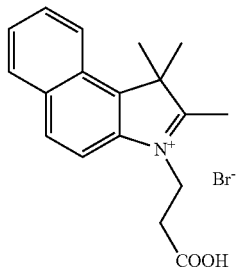

Results of Analyses:

[1] $^1$H-NMR (in DMSO-$d_6$) (chemical shift (ppm), multiplicity, number of protons of the peak top): (1.88, s, 6H), (2.12, s, 3H), (2.27, t, 2H), (3.47, s, 3H), (3.88, d, 1H), (4.05, d, 1H), (4.45, t, 2H), (6.42, dd, 2H), (6.50, d, 2H), (6.70, t, 1H), (7.20-7.26, m, 4H), (7.26, t, 2H), (7.44-7.58, m, 5H), (7.73-7.80, m, 2H), (8.00-8.08, m, 4H), (8.23, d, 1H), (8.50-8.56, m, 2H), (8.63, t, 1H)

[2] UV absorption (in methanol): $\lambda_{max}$=685.0 nm; $\epsilon$=1.59× $10^5 M^{-1}cm^{-1}$

[3] Decomposition point: 190° C.

Example 20

Preparation of Compound No. 43 in Iodide Form

A nitrogen-purged reaction flask was charged with 0.6 g of a compound of [Formula 44] shown below, 0.2 g of 1,1,3,3-tetramethoxypropane, and 1.3 g of pyridine, followed by stirring at 120° C. for 3.5 hours. Subsequently, 0.2 g of sodium iodide, 10 ml of chloroform, and 10 ml of water were added to the reaction mixture to conduct salt exchange. The aqueous layer was discarded, the solvent was removed by evaporation, and the residue was purified by silica gel column chromatography, followed by silica gel thin layer chromatography to give 30 mg (5%) of bluish purple powder, which was identified to be compound No. 43 in iodide form. The results of analyses on the resulting bluish purple powder are shown below.

[Formula 44]

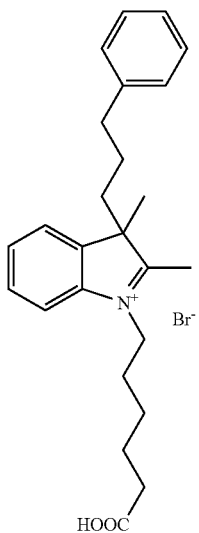

Results of Analyses:

[1] $^1$H-NMR (in CDCl$_3$) (chemical shift (ppm), multiplicity, number of protons of the peak top): (7.90, t, 1H), (7.67, t, 1H), (7.39-7.36, m, 2H), (7.25-6.99, m, 17H), (6.53-6.35, m, 2H), (4.09, t, 4H), (2.58-2.34, m, 8H), (1.81-1.45, m, 12H), (1.37-1.27, m, 8H), (0.89, quin, 4H)

[2] UV absorption (in methanol): $\lambda_{max}$=649.5 nm; $\epsilon$=1.30× 10$^5$ M$^{-1}$cm$^{-1}$

[3] Decomposition point: 241° C.

Example 21

Preparation of Compound No. 44 in Bromide Form

A nitrogen-purged reaction flask was charged with 2.2 g of a compound of [Formula 45] 1.5 g of a compound of [Formula 46], 0.5 g of acetic anhydride, and 5 g of pyridine, followed by stirring at 80° C. for 5 hours. The reaction mixture was poured into 100 ml of water, and the solid thus precipitated was purified by silica gel column chromatography to yield 240 mg (10%) of purple powder. The purple powder was identified to be compound No. 44 of bromide form. The results of analyses on the resulting purple powder are shown below.

[Formula 45]

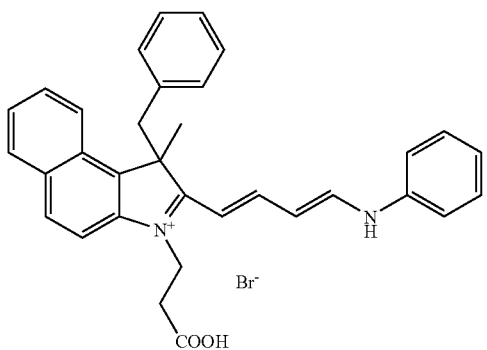

[Formula 46]

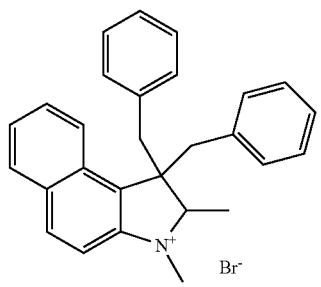

Results of Analyses:

[1] $^1$H-NMR (in DMSO-d$_6$) (chemical shift (ppm.), multiplicity, number of protons of the peak top): (2.06-2.15, m, 2H), (2.18, s, 3H), (3.22, s, 3H), (3.90-4.28, m, 8H), (6.40, d, 2H), (6.47-6.54, m, 6H), (677-6.99, m, 10H), (7.28, d, 1H), (7.50-7.60, m, 3H), (7.74, t, 1H), (7.84, t, 1H), (7.95, d, 1H), (8.02-8.07, m, 3H), (8.50, d, 1H), (8.75-8.90, m, 3H)

[2] UV absorption (in methanol): $\lambda_{max}$=697.0 nm; $\epsilon$=2.01× 10$^5$ M$^{-1}$cm$^{-1}$

[3] Decomposition point: 185° C.

Example 22

Preparation of Compound No. 45 in Hexafluorophosphate Form

A nitrogen-purged reaction flask was charged with 290 mg of a compound of [Formula 47] shown below, 46 mg of 4-mercaptobenzoic acid, and 1.0 g of acetonitrile, and 36 mg of triethylamine was added thereto dropwise while cooling on an ice bath. After stirring for 1 hour, 10 ml of ethyl acetate and 10 ml of water were added to conduct oil/water separation. The solvent was removed by evaporation, and 2 ml of acetone and 20 ml of n-hexane were added to the residue for reprecipitation to give 260 mg (79%) of brown powder, which was identified to be compound No. 45 in hexafluorophosphate form. The results of analyses on the resulting brown powder are shown below.

[Formula 47]

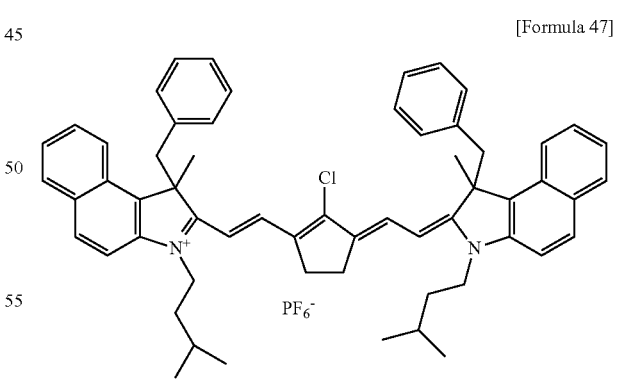

Results of Analyses:

[1] $^1$H-NMR (in DMSO-d$_6$) (chemical shift (ppm), multiplicity, number of protons of the peak top): (8.42, d, 2H), (8.21, d, 2H), (8.06, d, 2H), (8.01, d, 2H), (7.90, d, 2H), (7.72, t, 2H), (7.59, d, 2H), (7.54, t, 2H), (7.44, d, 2H), (6.93, t, 2H), (6.80, t, 2H), (6.17-6.13, m, 6H), (4.00-3.97, m, 6H), (3.12, s, 2H), (1.92, s, 6H), (1.49-1.42, m, 2H), (0.94, q, 4h), (0.86, d, 12H)

[2] UV absorption (in methanol): $\lambda_{max}$=870.0 nm; $\epsilon$=2.88× $10^5$ $M^{-1}cm^{-1}$

[3] Decomposition point: 190° C.

Example 23

Preparation of Compound No. 46 in Bromide Form

A nitrogen-purged reaction flask was charged with 21.2 g of a compound of [Formula 48], 22.8 g of a compound of [Formula 49], 10.1 g of triethylamine, and 86.4 g of acetonitrile, followed by stirring at 70° C. for 4 hours. The reaction mixture was cooled to room temperature, and the crystals thus precipitated were collected by filtration and heat-refluxed in 200 ml of ethyl acetate to yield 18.4 g (66%) of yellow powder, which was identified to be compound No. 46 in bromide form. The results of analyses on the resulting yellow powder are shown below.

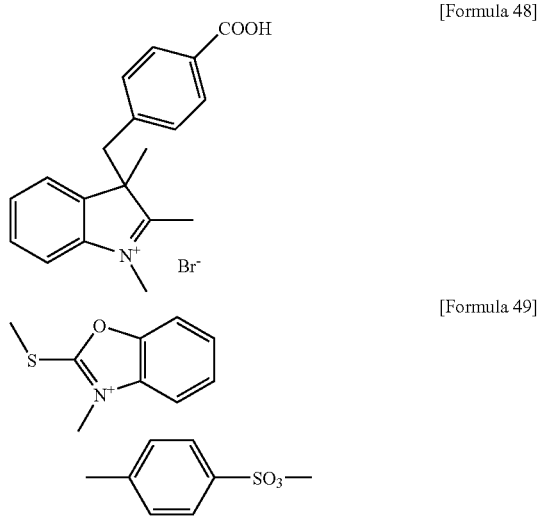

[Formula 48]

[Formula 49]

Results of Analyses:

[1] $^1$H-NMR (in DMSO-$d_6$) (chemical shift (ppm), multiplicity, number of protons of the peak top): (8.43, d, 1H), (8.04, d, 1H), (7.95, d, 2H), (7.82, d, 1H), (7.74, t, 1H), (7.59-7.52, m, 3H), (7.42, d, 1H), (7.27, d, 1H), (6.44, d, 2H), (5.72, s, 1H), (4.26, s, 1H), (3.98, s, 3H), (3.91, d, 1H), (3.46, s, 3H), (2.16, s, 3H)

[2] UV absorption (in methanol) $\lambda_{max}$=419.5 nm; $\epsilon$=4.48× $10^4$ $M^{-1}cm^{-1}$

[3] Decomposition point: 227° C.

Example 24

Preparation of Compound No. 46 in Tetrafluoroborate Form

In a nitrogen-purged reaction flask, 1.0 g of compound No. 46 bromide obtained in Example 23 was dissolved in 80 ml of methanol, and 20 ml of a methanol solution containing 0.3 g of sodium tetrafluoroborate was added thereto, followed by stirring for 2.5 hours. The solid thus precipitated was collected by filtration and washed with water to yield 0.1 g (10%) of yellow powder, which was identified to be compound No. 46 in tetrafluoroborate form. The results of analyses on the resulting yellow powder are shown below.

Results of Analyses:

[1] $^1$H-NMR (in DMSO-$d_6$) (chemical shift (ppm), multiplicity, number of protons of the peak top): (8.42, d, 1H), (8.04, d, 1H), (7.96, d, 2H), (7.71, d, 1H), (7.74, t, 1H), (7.61-7.40, m, 3H), (7.42, d, 1H), (7.26, d, 2H), (6.42, d, 2H), (5.75, s, 1H), (4.22, s, 1H), (3.97, s, 3H), (3.91, d, 1H), (3.46, s, 3H), (2.12, s, 3H)

[2] UV absorption (in methanol): $\lambda_{max}$=420.0 nm; $\epsilon$=4.39× $10^4$ $M^{-1}cm^{-1}$

[3] Decomposition point: 255° C.

Example 25

Preparation of Compound No. 46 in Cobalt Complex Salt Form 1

In a nitrogen-purged reaction flask were put 2.8 g of compound No. 46 bromide obtained in Example 23, 4.1 g of a compound of [Formula 50], and 40 g of 2,2,3,3-tetrafluoropropanol, followed by stirring at 60° C. for 2 hours. To the reaction system was added 5 ml of ethyl acetate for crystallization to afford 3.7 g (61%) of brown powder, which was identified to be compound No. 46 of cobalt complex salt form 1. The results of analyses on the resulting brown powder are shown below.

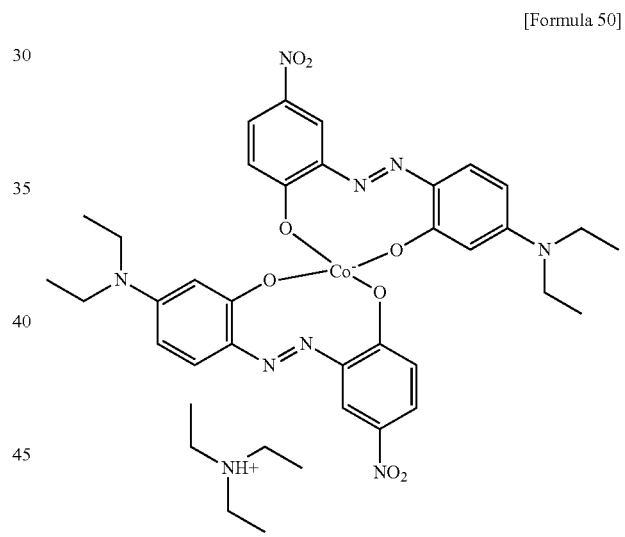

[Formula 50]

Results of Analyses:

[1] $^1$H-NMR (in DMSO-$d_6$) (chemical shift (ppm), multiplicity, number of protons of the peak top): (8.99, s, 2H), (8.45, d, 1H), (8.05, d, 1H), (7.98, d, 2H), (7.86-7.81, m, 3H), (7.75, t, 1H), (7.66-7.53, m, 5H), (7.43, d, 1H), (7.35, d, 2H), (6.60-6.54, m, 4H), (3.46, s, 3H), (3.32-3.27, m, 11H), (1.10, t, 12H)

[2] UV absorption (in methanol): $\lambda_{max}$=423.5 nm; $\epsilon$=7.68× $10^4$ $M^{-1}cm^{-1}$

[3] Decomposition point: 261° C.

Example 26

Preparation of Compound No. 46 in Cobalt Complex Salt Form 2

In a nitrogen-purged reaction flask were put 0.5 g of compound No. 46 bromide obtained in Example 23, 0.9 g of a compound of [Formula 51], and 10 g of 2,2,3,3-tetrafluoropropanol, followed by stirring at 60° C. for 1.5 hours. To the reaction system was added 10 ml of ethyl acetate for crystallization to afford 1.1 g (90%) of brown powder, which was identified to be compound No. 46 of cobalt complex salt form 2. The results of analyses on the resulting brown powder are shown below.

[Formula 51]

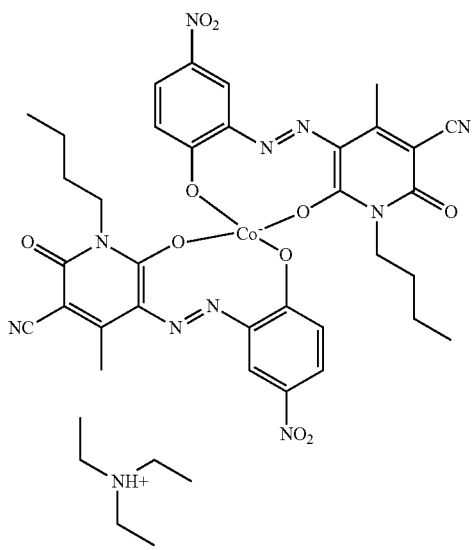

Results of Analyses:

[1] $^1$H-NMR (in DMSO-$d_6$) (chemical shift (ppm), multiplicity, number of protons of the peak top): (9.02, s, 2H), (8.45, d, 1H), (8.06, d, 1H), (8.00-7.93, m, 4H), (7.83, d, 1H), (7.75, t, 1H), (7.63-7.54, m, 3H), (7.44, d, 1H), (7.36, d, 2H), (6.89, d, 2H), (6.58, d, 2H), (5.76, s, 1H), (4.32, s, 1H), (3.99-3.96, m, 411), (3.59-3.48, m, 7H), (2.89, s, 6H), (2.17, s, 3H), (0.92, quin, 4H), (0.76, sex, 4H), (0.45, t, 6H)

[2] UV absorption (in acetone): $\lambda_{max}$=417.5 nm; $\epsilon$=7.11× $10^4 M^{-1}cm^{-1}$

[3] Decomposition point: 266° C.

Evaluation Example 2 and Comparative Evaluation Example 2

A 10 μm-thick aluminum film was formed on a 200 μm-thick, 20 mm by 20 mm polycarbonate sheet by evaporation deposition. Compound No. 46 of cobalt complex salt form 2 was dissolved in 2,2,3,3-tetrafluoropropanol to prepare a 1 mass % solution. The solution was applied to the aluminum film of the polycarbonate sheet by spin coating at 2000 rpm for 60 seconds to prepare a specimen. A comparative specimen as prepared in the same manner, except for replacing compound No. 46 of cobalt complex form 2 with comparative compound 1 shown below. The resulting specimens were each immersed in 80° C. water for 30 seconds. The reflectance (R) of the specimen was measured before and after the immersion at $\lambda_{max}$ of 405 nm. The difference between the reflectance before the immersion ($R_1$) and that after the immersion ($R_2$) ($\Delta R = R_2 - R_1$) was taken as a measure for affinity to a metallic reflective film. The results obtained are shown in Table 2.

[Formula 52]

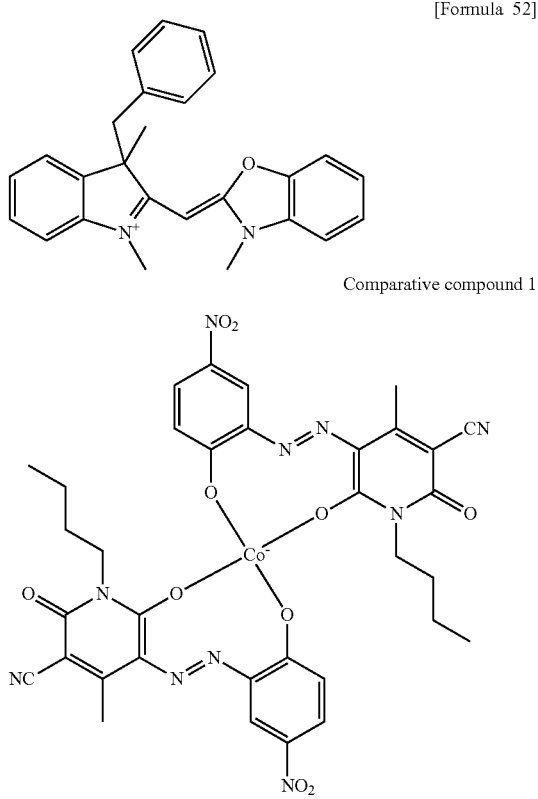

Comparative compound 1

TABLE 2

|  | 405 nm |
|---|---|
| Evaluation Example 2 | 0.3% |
| Comparative Evaluation Example 2 | 17.1% |

The results in Table 2 show that the metal reflective film having the cyanine compound of the invention thereon undergoes little change in reflectance on immersion in 80° C. water, proving highly water-resistant. In contrast, the metal reflective film having the comparative compound thereon underwent a reflectance change of more than 10%, proving to have poor water resistance. This is considered to be because the cyanine compound of the invention has high affinity for a metallic reflective film owing to its anchor groups.

The cyanine compound of the invention exhibits high affinity for a metallic reflective film at a wavelength of 405 nm, the laser wavelength used for HDDVD-Rs and BD-Rs, and is therefore suited as an optical recording material.

Evaluation Examples 3 to 6 and Comparative Evaluation Examples 3 to 5

Each of the cyanine compounds shown in Table 3 below was dissolved in 2,2,3,3-tetrafluoropropanol to prepare a 1 mass % solution. The solution was applied to a 25 mm by 25 mm polycarbonate sheet by spin coating at 2000 rpm for 60 seconds to prepare a specimen. The resulting specimen was immersed in 78° C. water for 1 minute. The absorbance (R) of the specimen at the $\lambda_{max}$ was measured before and after the immersion. Percent retention (X) of the absorbance was calculated from the absorbance before the immersion ($R_1$) and that after the immersion ($R_2$) ($X=(R_1-R_2)/R_1$), which was taken as a measure for resistance of the coating film to elution with water. The results obtained are shown in Table 3.

TABLE 3

| | Cyanine Compound | Absorption Maximum (nm) | Percent Retention (%) |
|---|---|---|---|
| Evaluation Example 3 | compound No. 1 iodide | 621 | 72.1 |
| Comp. Evaluation Example 3 | comparative compound 1 | 622 | 5.9 |
| Evaluation Example 4 | compound No. 38 iodide | 690 | 70.6 |
| Evaluation Example 5 | compound No. 43 iodide | 684 | 85.3 |
| Comp. Evaluation Example 4 | comparative compound 2 | 697 | 3.1 |
| Evaluation Example 6 | compound No. 39 iodide | 690 | 92.4 |
| Comp. Evaluation Example 5 | comparative compound 3 | 702 | 83.8 |

[Formula 53]

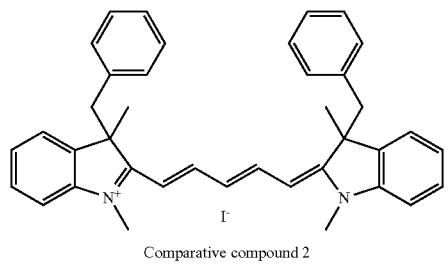 [SMILES: CN1/C(=C/C=C/C=C/C2=[N+](C)c3ccccc3C2(C)Cc2ccccc2)C(C)(Cc2ccccc2)c2ccccc21 ; [I-]]

Comparative compound 2

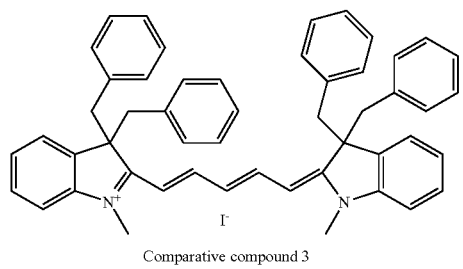 [SMILES: CN1/C(=C/C=C/C=C/C2=[N+](C)c3ccccc3C2(Cc2ccccc2)Cc2ccccc2)C(Cc2ccccc2)(Cc2ccccc2)c2ccccc21 ; [I-]]

Comparative compound 3

Evaluation Example 7 and Comparative Evaluation Example 6

Specimens were prepared in the same manner as in Evaluation Examples 3 to 6, except for using the cyanine compounds of Table 4. Each specimen was immersed in water at 18° C. for 10 seconds. Percent retention X was obtained from the absorbance at the $\lambda_{max}$ before the immersion ($R_1$) and that after the immersion ($R_2$) ($X=(R_1-R_2)/R_1$), which was taken as a measure for resistance of the coating film to elution with water. The results obtained are shown in Table 4.

TABLE 4

| | Cyanine Compound | Absorption Maximum (nm) | Percent Retention (%) |
|---|---|---|---|
| Evaluation Example 7 | compound No. 46 tetrafluoroborate | 425 | 66.7 |
| Comp. Evaluation Example 6 | comparative compound 4 | 430 | 5.6 |

[Formula 54]

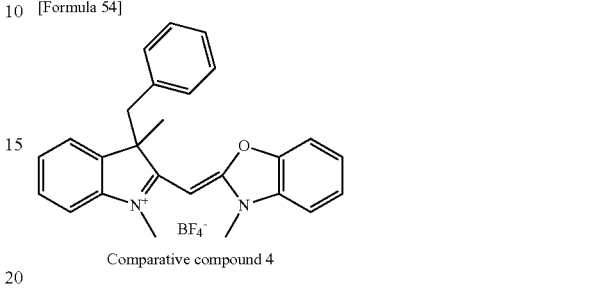

Comparative compound 4

The results in Tables 3 and 4 prove that a thin film formed of the cyanine compound of the invention on a polycarbonate substrate has a higher retention of absorbance than a thin film formed of the comparative compound when immersed in water at 80° C. or 18° C. This is considered to be because of the affinity between the carboxyl group, which functions as an anchor group, of the cyanine compound of the invention and the polar group of the polycarbonate.

INDUSTRIAL APPLICABILITY

The present invention provides a cyanine compound having absorption wavelength characteristics suited for use as an optical element and high affinity for a metal or a resin. An optical filter formed by using the cyanine compound is suitable for application to image displays, and an optical recording material containing the cyanine compound is suitable to form an optical recording layer of an optical recording medium.

The invention claimed is:
1. An optical filter comprising at least one cyanine compound of general formula (VI):

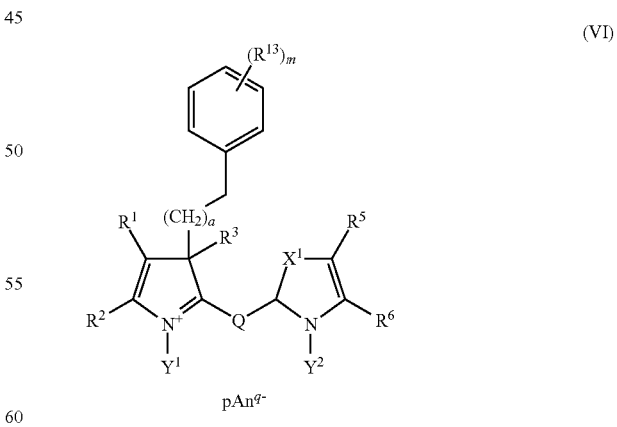

(VI)

wherein $R^3$ each represents an optionally substituted alkyl group having 1 to 10 carbon atoms, or an optionally substituted arylalkyl group having 7 to 30 carbon atoms
$R^1$ and $R^2$, and $R^5$ and $R^6$, together form a a benzene or naphthalene ring;
$X^1$ represents an oxygen atom, or —$CR^7R^8$—

$R^7$ and $R^8$ in $X^1$ each independently represent an optionally substituted alkyl group having 1 to 10 carbon atoms, or an optionally substituted arylalkyl group having 7 to 30 carbon atoms;

$Y^1$ and $Y^2$ each independently represent an optionally substituted alkyl group having 1 to 10 carbon atoms, or an anchor group represented by general formula (IX)

-L-COOH  (IX)

wherein L represents a single bond or a divalent hydrocarbon group having 1 to 12 carbon atoms, with the proviso that at least one of $Y^1$ and $Y^2$ is an anchor group;

-Q- represents a linking group comprising a polymethine chain optionally containing a cyclic structure, the polymethine chain may have its hydrogen atom replaced by a halogen atom, a cyano group, a hydroxyl group, an alkyl group, an alkoxy group, or an aryl group, of which the alkyl, alkoxy or aryl group may further be substituted with a halogen atom, a cyano group, a hydroxyl group, an alkyl group, an alkoxy group, or an aryl group;

$An^{q-}$ represents a q-valent anion;

a represents a number of 0 to 4;

q represents 1 or 2; and p represents a number necessary to neutralize the electric charge;

$R^{13}$, each of which may be the same or different, represents a cyano group, a carboxyl group, or adjacent $R^{13}$s may be connected to each other to form a benzene ring; and m represents a number of 0 to 5.

2. The optical filter according to claim 1, wherein the polymethine chain composing the linking group as represented by -Q- is selected from monomethine, trimethine, pentamethine, and heptamethine.

3. The optical filter according to claim 1, configured for an image display.

4. The optical filter according to claim 3, wherein the image display is a plasma display.

5. The optical filter according to claim 1, wherein the cyanine compound is selected from the group consisting of:

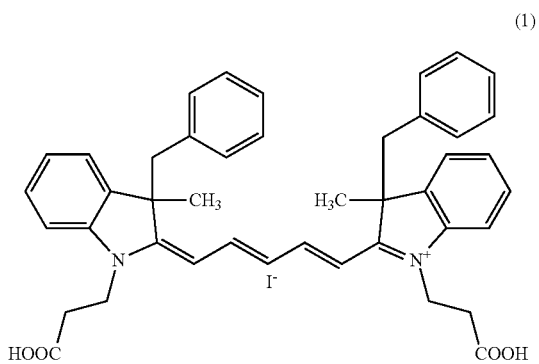 [SMILES: CC1(Cc2ccccc2)C(/C=C/C=C/C=C2/N(CCC(=O)O)c3ccccc3C2(C)Cc2ccccc2)=[N+](CCC(=O)O)c2ccccc21 ; [I-]]

(1)

and

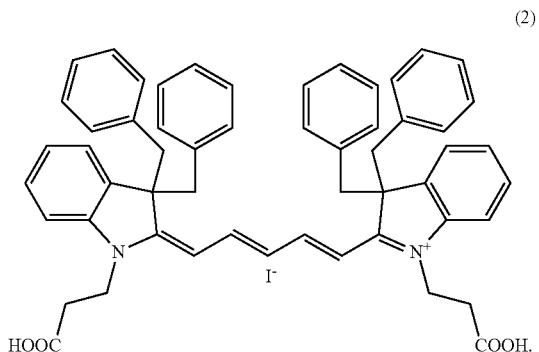 [SMILES: O=C(O)CCN1/C(=C/C=C/C=C/C2=[N+](CCC(=O)O)c3ccccc3C2(Cc2ccccc2)Cc2ccccc2)C(Cc2ccccc2)(Cc2ccccc2)c2ccccc21 ; [I-]]

(2)

6. The optical filter according to claim 1, wherein each of $Y^1$ and $Y^2$ is an anchor group.

* * * * *